(12) United States Patent
Komorowski et al.

(10) Patent No.: US 12,324,796 B2
(45) Date of Patent: *Jun. 10, 2025

(54) SLEEP-IMPROVING COMPOSITIONS AND METHODS OF USE

(71) Applicant: Bonafide Health, LLC, Harrison, NY (US)

(72) Inventors: James R. Komorowski, Trumbull, CT (US); Devon Bernsley, New York, NY (US)

(73) Assignee: Bonafide Health, LLC, Harrison, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/022,909

(22) Filed: Jan. 15, 2025

(65) Prior Publication Data

US 2025/0152544 A1 May 15, 2025

Related U.S. Application Data

(63) Continuation of application No. 18/665,149, filed on May 15, 2024, now Pat. No. 12,239,623.

(60) Provisional application No. 63/466,498, filed on May 15, 2023.

(51) Int. Cl.
| | | |
|---|---|---|
| A61K 31/198 | (2006.01) |
| A61K 31/197 | (2006.01) |
| A61K 31/235 | (2006.01) |
| A61K 31/685 | (2006.01) |
| A61K 31/7076 | (2006.01) |
| A61K 33/06 | (2006.01) |
| A61P 25/20 | (2006.01) |

(52) U.S. Cl.
CPC .......... *A61K 31/198* (2013.01); *A61K 31/197* (2013.01); *A61K 31/235* (2013.01); *A61K 31/685* (2013.01); *A61K 31/7076* (2013.01); *A61K 33/06* (2013.01); *A61P 25/20* (2018.01)

(58) Field of Classification Search
None
See application file for complete search history.

(56) References Cited

U.S. PATENT DOCUMENTS

| | | |
|---|---|---|
| 2015/0087679 A1 | 3/2015 | Helmi et al. |
| 2015/0367366 A1 | 12/2015 | Edwards et al. |
| 2017/0020815 A1 | 1/2017 | Gutierrez et al. |
| 2019/0038573 A1 | 2/2019 | Westphal et al. |
| 2020/0246404 A1 | 8/2020 | Yucel et al. |

FOREIGN PATENT DOCUMENTS

WO 2024/238657 A2 11/2024

OTHER PUBLICATIONS

PCT/US2024/029467 International Search Report and Written Opinion mailed Nov. 20, 2024.

*Primary Examiner* — Bethany P Barham
*Assistant Examiner* — Peter Anthopolos
(74) *Attorney, Agent, or Firm* — Arnall Golden Gregory LLP

(57) ABSTRACT

Disclosed herein are compositions comprising two or more sleep-inducing agonists and/or a sleep-inducing antagonist. The compositions are for promoting healthy sleep quality and treating, ameliorating, preventing, or reducing one or more symptoms associated with menopause. Also described herein are methods utilizing the aforementioned compositions.

25 Claims, 15 Drawing Sheets

SLEEP-IMPROVING COMPOSITIONS AND METHODS OF USE

CROSS-REFERENCE TO RELATED APPLICATIONS

This application is a continuation of U.S. patent application Ser. No. 18/665,149 filed May 15, 2024, which claims the benefit of U.S. Provisional Application No. 63/466,498 filed May 15, 2023, the disclosure of which is incorporated herein by reference in their entirety.

BACKGROUND

Insomnia and poor sleep quality are conditions that affect up to 70 million Americans every year. Women have a lifetime risk of insomnia and poor sleep quality that is as much as 40% higher than that of men. The conditions in women are exacerbated during menopause as a decrease in estrogen concentrations leads to several symptoms associated with menopause, including night sweats that result in a decrease in both sleep duration and quality. Menopausal women report more nightly disturbances in their normal routine than premenopausal women, with common reports of waking up earlier than planned, trouble falling asleep, and trouble staying asleep.

There are numerous prescription drug treatment options for insomnia and poor sleep quality, including Valium, Xanax, Klonopin, Zopiclone, Zaleplon, Zolpidem, and Eszopiclone. These prescription drugs have been associated with negative side effects, such as headaches, dizziness, dry mouth, nausea, impaired cognition, and higher fall risks in older populations, all of which are particularly problematic in patient populations prone to these symptoms, such as those going through menopause. There are also over-the-counter treatment options, among which, melatonin is the most common one. However, melatonin also has side effects, including vivid dreams, nightmares, dizziness, daytime sleepiness, headache, stomach cramps, depression, and irritability.

Therefore, there is a need to develop safe and effective treatment options for improving sleep quality.

SUMMARY

Embodiments of the present disclosure relate to novel compositions and their use in promoting healthy sleep quality and treating, ameliorating, preventing, or reducing one or more symptoms associated with menopause.

These and other features, aspects, and advantages of the present embodiments will become understood with reference to the following description, appended claims, and accompanying figures.

DETAILED DESCRIPTION

Figure 1A:
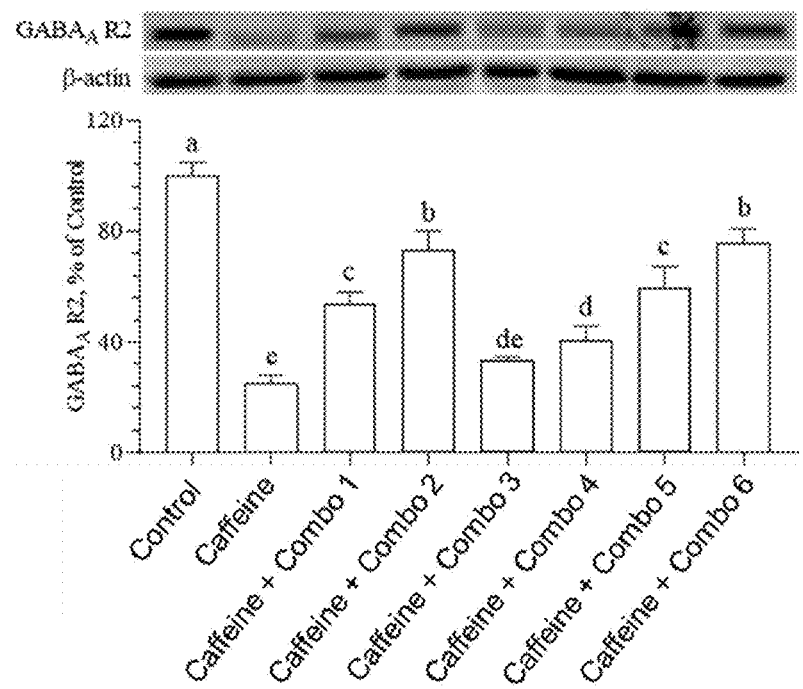
FIG. 1A shows the percentage of GABAA receptor 2 in mice treated with:
(i) control;
(ii) caffeine (7.5 mg/kg);
(iii) a combination of 100 mg HED of magnesium glycinate, 200 mg HED of L-theanine, and 300 mg HED of GABA (Combo 1) together with 7.5 mg/kg caffeine;
(iv) a combination of caffeine, 100 mg HED of magnesium glycinate, 200 mg HED of L-theanine, 300 mg HED of GABA, and 412 mg HED of combined amount of S-adenosyl-L-methionine (SAMe) and propyl gallate (Combo 2) together with 7.5 mg/kg caffeine;
(v) a combination of 100 mg HED of magnesium glycinate, 200 mg HED of L-theanine, and 412 mg HED of combined SAMe and propyl gallate (Combo 3) together with 7.5 mg/kg caffeine;
(vi) a combination of 100 mg HED of magnesium glycinate, 200 mg HED of L-theanine, 412 mg HED of combined SAMe and propyl gallate, and 100 mg HED of phosphatidyl serine (Combo 4) together with 7.5 mg/kg caffeine;
(vii) a combination of 100 mg HED of magnesium glycinate, 200 mg HED of L-theanine, 300 mg HED of GABA, and 100 mg HED of phosphatidyl serine (Combo 5) together with 7.5 mg/kg caffeine; or
(viii) a combination of 100 mg HED of magnesium glycinate, 200 mg HED of L-theanine, 300 mg HED of GABA, 412 mg HED of combined SAMe and propyl gallate, and 100 mg HED of phosphatidyl serine (Combo 6) together with 7.5 mg/kg caffeine.

Described herein are novel compositions each comprising two or more sleep-inducing agonists. In certain embodiments, a composition can be comprised of a first sleep-inducing agonist and a second sleep-inducing agonist, wherein the first sleep-inducing agonist is different than the second sleep-inducing agonist. An example of the first sleep-inducing agonist is L-theanine and an example of the second sleep-inducing agonist is a magnesium salt. In certain embodiments, a composition can be comprised of a first sleep-inducing agonist, a second sleep-inducing agonist, and a third sleep-inducing agonist, wherein the first sleep-inducing agonist, the second sleep-inducing agonist, and the third sleep-inducing agonist differ from each other. An example of the first sleep-inducing agonist is L-theanine, an example of the second sleep-inducing agonist is a magnesium salt, and an example of the third sleep-inducing agonist is gamma-aminobutyric acid (GABA). The number of sleep-inducing agonists in a composition is not particularly limited. For example, a composition can comprise one, two, three, four, five, six, or more sleep-inducing agonists that are different from each other. Examples of a salt include but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, glycinate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

When provided in a composition as described herein, the amount of each sleep-inducing agonist in the composition may be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of sleep-inducing agonists to each other in the composition may be present in a synergistic ratio.

As used herein, a "synergistic ratio" refers to a ratio that elicits an unexpectedly superior pharmacological, physiological, nutritional, or nutraceutical effect in a subject. The synergistic ratio is not particularly limited, although the combination of compounds set forth herein or components that are capable of achieving synergistic effects as defined herein, which would be immediately envisaged by the skilled artisan in view of the claim terms and surrounding context of the terms.

For example, in a composition comprising a first sleep-inducing agonist, a second sleep-inducing agonist, and a third sleep-inducing agonist, the synergistic ratio of the first sleep-inducing agonist to the second sleep-inducing agonist to the third sleep-inducing agonist may be about 1:1:1, 1:1:2, 1:1:3, 1:1:4, 1:1:5, 1:1:6, 1:1:7, 1:1:8, 1:1:9, 1:1:10, 1:2:1, 1:2:2, 1:2:3, 1:2:4, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1, 2:1:2, 2:1:3, 2:1:4, 2:1:5, 2:1:6, 2:1:7, 2:1:8, 2:1:9, 2:1:10, 2:2:1, 2:2:2, 2:2:3, 2:2:4, 2:2:5, 2:2:6, 2:2:7, 2:2:8, 2:2:9, 2:2:10, 2:3:1, 2:3:2, 2:3:3, 2:3:4, 2:3:5, 2:3:6, 2:3:7, 2:3:8, 2:3:9, 2:3:10, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1, 3:1:2, 3:1:3, 3:1:4, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1, 4:1:2, 4:1:3, 4:1:4, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1, 5:1:2, 5:1:3, 5:1:4, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, or any ratio in between. In view of the results and discussion contained herein, one of skill in the art would understand how to formulate a composition comprising two or more sleep-inducing agonists, as described herein, to achieve the results described herein.

In some embodiments, the composition, as described herein, may further comprise a sleep-inducing antagonist and/or a gallic acid ester. An example of the sleep-inducing antagonist is S-adenosyl L-methionine (SAMe) and an example of the gallic acid ester is propyl gallate. The amount of the sleep-inducing antagonist in the composition may be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425µ, 450µ, 475µ, 500µ, 525µ, 575µ, 600µ, 625µ, 650µ, 675µ, 700µ, 725µ g, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of the gallic acid ester in the composition may be about 10 µg, 15 µg, 20 µg, 25 µg, 30 µg, 35 µg, 40 µg, 45 µg, 50 µg, 55 µg, 60 µg, 65 µg, 70 µg, 75µ, 80µ, 85µ, 90µ, 95µ, 100µ, 125µ, 150µ, 175µ, 200µ, 225µ, 250µ, 275µ, 300µ, 325µ, 350µ, 375µ, 400µ, 425µ, 450µ, 475µ, 500µ, 525µ, 575µ, 600µ, 625µ g, 650µ, 675µ, 700µ, 725µ, 750µ, 775µ, 800µ, 825µ, 850µ, 875µ, 900µ, 925µ g, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, or more, or any value in between. The amount of each sleep-inducing agonist to the combined amount of the sleep-inducing antagonist and the gallic acid ester may be present in a synergistic ratio in the composition described herein. For example, in a composition comprising a first sleep-inducing agonist, a second sleep-inducing agonist, and a combination of a sleep-inducing antagonist and a gallic acid ester, the synergistic ratio of the amount of the first sleep-inducing agonist to the amount of the second sleep-inducing agonist to the combined amount of the sleep-inducing antagonist and the gallic acid ester may be about 1:1:1, 1:1:2, 1:1:3, 1:1:4, 1:1:5, 1:1:6, 1:1:7, 1:1:8, 1:1:9, 1:1:10, 1:2:1, 1:2:1.5, 1:2:1.59, 1:2:2, 1:2:3, 1:2:4, 1:2:4.12, 1:2:5, 1:2:6, 1:2:7, 1:2:8, 1:2:9, 1:2:10, 1:3:1, 1:3:2, 1:3:3, 1:3:4, 1:3:5, 1:3:6, 1:3:7, 1:3:8, 1:3:9, 1:3:10, 1:4:1, 1:4:2, 1:4:3, 1:4:4, 1:4:5, 1:4:6, 1:4:7, 1:4:8, 1:4:9, 1:4:10, 1:5:1, 1:5:2, 1:5:3, 1:5:4, 1:5:5, 1:5:6, 1:5:7, 1:5:8, 1:5:9, 1:5:10, 1:6:1, 1:6:2, 1:6:3, 1:6:4, 1:6:5, 1:6:6, 1:6:7, 1:6:8, 1:6:9, 1:6:10, 1:7:1, 1:7:2, 1:7:3, 1:7:4, 1:7:5, 1:7:6, 1:7:7, 1:7:8, 1:7:9, 1:7:10, 1:8:1, 1:8:2, 1:8:3, 1:8:4, 1:8:5, 1:8:6, 1:8:7, 1:8:8, 1:8:9, 1:8:10, 1:9:1, 1:9:2, 1:9:3, 1:9:4, 1:9:5, 1:9:6, 1:9:7, 1:9:8, 1:9:9, 1:9:10, 1:10:1, 1:10:2, 1:10:3, 1:10:4, 1:10:5, 1:10:6, 1:10:7, 1:10:8, 1:10:9, 1:10:10, 2:1:1, 2:1:2, 2:1:3, 2:1:4, 2:1:5, 2:1:6, 2:1:7, 2:1:8, 2:1:9, 2:1:10, 2:2:1, 2:2:2, 2:2:3, 2:2:4, 2:2:5, 2:2:6, 2:2:7, 2:2:8, 2:2:9, 2:2:10, 2:3:1, 2:3:2, 2:3:3, 2:3:4, 2:3:5, 2:3:6, 2:3:7, 2:3:8, 2:3:9, 2:3:10, 2:4:1, 2:4:2, 2:4:3, 2:4:4, 2:4:5, 2:4:6, 2:4:7, 2:4:8, 2:4:9, 2:4:10, 2:5:1, 2:5:2, 2:5:3, 2:5:4, 2:5:5, 2:5:6, 2:5:7, 2:5:8, 2:5:9, 2:5:10, 2:6:1, 2:6:2, 2:6:3, 2:6:4, 2:6:5, 2:6:6, 2:6:7, 2:6:8, 2:6:9, 2:6:10, 2:7:1, 2:7:2, 2:7:3, 2:7:4, 2:7:5, 2:7:6, 2:7:7, 2:7:8, 2:7:9, 2:7:10, 2:8:1, 2:8:2, 2:8:3, 2:8:4, 2:8:5, 2:8:6, 2:8:7, 2:8:8, 2:8:9, 2:8:10, 2:9:1, 2:9:2, 2:9:3, 2:9:4, 2:9:5, 2:9:6, 2:9:7, 2:9:8, 2:9:9, 2:9:10, 2:10:1, 2:10:2, 2:10:3, 2:10:4, 2:10:5, 2:10:6, 2:10:7, 2:10:8, 2:10:9, 2:10:10, 3:1:1, 3:1:2, 3:1:3, 3:1:4, 3:1:5, 3:1:6, 3:1:7, 3:1:8, 3:1:9, 3:1:10, 3:2:1, 3:2:2, 3:2:3, 3:2:4, 3:2:5, 3:2:6, 3:2:7, 3:2:8, 3:2:9, 3:2:10, 3:3:1, 3:3:2, 3:3:3, 3:3:4, 3:3:5, 3:3:6, 3:3:7, 3:3:8, 3:3:9, 3:3:10, 3:4:1, 3:4:2, 3:4:3, 3:4:4, 3:4:5, 3:4:6, 3:4:7, 3:4:8, 3:4:9, 3:4:10, 3:5:1, 3:5:2, 3:5:3, 3:5:4, 3:5:5, 3:5:6, 3:5:7, 3:5:8, 3:5:9, 3:5:10, 3:6:1, 3:6:2, 3:6:3, 3:6:4, 3:6:5, 3:6:6, 3:6:7, 3:6:8, 3:6:9, 3:6:10, 3:7:1, 3:7:2, 3:7:3, 3:7:4, 3:7:5, 3:7:6, 3:7:7, 3:7:8, 3:7:9, 3:7:10, 3:8:1, 3:8:2, 3:8:3, 3:8:4, 3:8:5, 3:8:6, 3:8:7, 3:8:8, 3:8:9, 3:8:10, 3:9:1, 3:9:2, 3:9:3, 3:9:4, 3:9:5, 3:9:6, 3:9:7, 3:9:8, 3:9:9, 3:9:10, 3:10:1, 3:10:2, 3:10:3, 3:10:4, 3:10:5, 3:10:6, 3:10:7, 3:10:8, 3:10:9, 3:10:10, 4:1:1, 4:1:2, 4:1:3, 4:1:4, 4:1:5, 4:1:6, 4:1:7, 4:1:8, 4:1:9, 4:1:10, 4:2:1, 4:2:2, 4:2:3, 4:2:4, 4:2:5, 4:2:6, 4:2:7, 4:2:8, 4:2:9, 4:2:10, 4:3:1, 4:3:2, 4:3:3, 4:3:4, 4:3:5, 4:3:6, 4:3:7, 4:3:8, 4:3:9, 4:3:10, 4:4:1, 4:4:2, 4:4:3, 4:4:4, 4:4:5, 4:4:6, 4:4:7, 4:4:8, 4:4:9, 4:4:10, 4:5:1, 4:5:2, 4:5:3, 4:5:4, 4:5:5, 4:5:6, 4:5:7, 4:5:8, 4:5:9, 4:5:10, 4:6:1, 4:6:2, 4:6:3, 4:6:4, 4:6:5, 4:6:6, 4:6:7, 4:6:8, 4:6:9, 4:6:10, 4:7:1, 4:7:2, 4:7:3, 4:7:4, 4:7:5, 4:7:6, 4:7:7, 4:7:8, 4:7:9, 4:7:10, 4:8:1, 4:8:2, 4:8:3, 4:8:4, 4:8:5, 4:8:6, 4:8:7, 4:8:8, 4:8:9, 4:8:10, 4:9:1, 4:9:2, 4:9:3, 4:9:4, 4:9:5, 4:9:6, 4:9:7, 4:9:8, 4:9:9, 4:9:10, 4:10:1, 4:10:2, 4:10:3, 4:10:4, 4:10:5, 4:10:6, 4:10:7, 4:10:8, 4:10:9, 4:10:10, 5:1:1, 5:1:2, 5:1:3, 5:1:4, 5:1:5, 5:1:6, 5:1:7, 5:1:8, 5:1:9, 5:1:10, 5:2:1, 5:2:2, 5:2:3, 5:2:4, 5:2:5, 5:2:6, 5:2:7, 5:2:8, 5:2:9, 5:2:10, 5:3:1, 5:3:2, 5:3:3, 5:3:4, 5:3:5, 5:3:6, 5:3:7, 5:3:8, 5:3:9, 5:3:10, 5:4:1, 5:4:2, 5:4:3, 5:4:4, 5:4:5, 5:4:6, 5:4:7, 5:4:8, 5:4:9, 5:4:10, 5:5:1, 5:5:2, 5:5:3, 5:5:4, 5:5:5, 5:5:6, 5:5:7, 5:5:8, 5:5:9, 5:5:10, 5:6:1, 5:6:2, 5:6:3, 5:6:4, 5:6:5, 5:6:6, 5:6:7, 5:6:8, 5:6:9, 5:6:10, 5:7:1, 5:7:2, 5:7:3, 5:7:4, 5:7:5, 5:7:6, 5:7:7, 5:7:8, 5:7:9, 5:7:10, 5:8:1, 5:8:2, 5:8:3, 5:8:4, 5:8:5, 5:8:6, 5:8:7, 5:8:8, 5:8:9, 5:8:10, 5:9:1, 5:9:2, 5:9:3, 5:9:4, 5:9:5, 5:9:6, 5:9:7, 5:9:8, 5:9:9, 5:9:10, 5:10:1, 5:10:2, 5:10:3, 5:10:4, 5:10:5, 5:10:6, 5:10:7, 5:10:8, 5:10:9, 5:10:10, 6:1:1, 6:1:2, 6:1:3, 6:1:4, 6:1:5, 6:1:6, 6:1:7, 6:1:8, 6:1:9, 6:1:10, 6:2:1, 6:2:2, 6:2:3, 6:2:4, 6:2:5, 6:2:6, 6:2:7, 6:2:8, 6:2:9, 6:2:10, 6:3:1, 6:3:2, 6:3:3, 6:3:4, 6:3:5, 6:3:6, 6:3:7, 6:3:8, 6:3:9, 6:3:10, 6:4:1, 6:4:2, 6:4:3, 6:4:4, 6:4:5, 6:4:6, 6:4:7, 6:4:8, 6:4:9, 6:4:10, 6:5:1, 6:5:2, 6:5:3, 6:5:4, 6:5:5, 6:5:6, 6:5:7, 6:5:8, 6:5:9, 6:5:10, 6:6:1, 6:6:2, 6:6:3, 6:6:4, 6:6:5, 6:6:6, 6:6:7, 6:6:8, 6:6:9, 6:6:10, 6:7:1, 6:7:2, 6:7:3, 6:7:4, 6:7:5, 6:7:6, 6:7:7, 6:7:8, 6:7:9, 6:7:10, 6:8:1, 6:8:2, 6:8:3, 6:8:4, 6:8:5, 6:8:6, 6:8:7, 6:8:8, 6:8:9, 6:8:10, 6:9:1, 6:9:2, 6:9:3, 6:9:4, 6:9:5, 6:9:6, 6:9:7, 6:9:8, 6:9:9, 6:9:10, 6:10:1, 6:10:2, 6:10:3, 6:10:4, 6:10:5, 6:10:6, 6:10:7, 6:10:8, 6:10:9, 6:10:10, 7:1:1, 7:1:2, 7:1:3, 7:1:4, 7:1:5, 7:1:6, 7:1:7, 7:1:8, 7:1:9, 7:1:10, 7:2:1, 7:2:2, 7:2:3, 7:2:4, 7:2:5, 7:2:6, 7:2:7, 7:2:8, 7:2:9, 7:2:10, 7:3:1, 7:3:2, 7:3:3, 7:3:4, 7:3:5, 7:3:6, 7:3:7, 7:3:8, 7:3:9, 7:3:10, 7:4:1, 7:4:2, 7:4:3, 7:4:4, 7:4:5, 7:4:6, 7:4:7, 7:4:8, 7:4:9, 7:4:10, 7:5:1, 7:5:2, 7:5:3, 7:5:4, 7:5:5, 7:5:6, 7:5:7, 7:5:8, 7:5:9, 7:5:10, 7:6:1, 7:6:2, 7:6:3, 7:6:4, 7:6:5, 7:6:6, 7:6:7, 7:6:8, 7:6:9, 7:6:10, 7:7:1, 7:7:2, 7:7:3, 7:7:4, 7:7:5, 7:7:6, 7:7:7, 7:7:8, 7:7:9, 7:7:10, 7:8:1, 7:8:2, 7:8:3, 7:8:4, 7:8:5, 7:8:6, 7:8:7, 7:8:8, 7:8:9, 7:8:10, 7:9:1, 7:9:2, 7:9:3, 7:9:4, 7:9:5, 7:9:6, 7:9:7, 7:9:8, 7:9:9, 7:9:10, 7:10:1, 7:10:2, 7:10:3, 7:10:4, 7:10:5, 7:10:6, 7:10:7, 7:10:8, 7:10:9, 7:10:10, 8:1:1, 8:1:2, 8:1:3, 8:1:4, 8:1:5, 8:1:6, 8:1:7, 8:1:8, 8:1:9, 8:1:10, 8:2:1, 8:2:2, 8:2:3, 8:2:4, 8:2:5, 8:2:6, 8:2:7, 8:2:8, 8:2:9, 8:2:10, 8:3:1, 8:3:2, 8:3:3, 8:3:4, 8:3:5, 8:3:6, 8:3:7, 8:3:8, 8:3:9, 8:3:10, 8:4:1, 8:4:2, 8:4:3, 8:4:4, 8:4:5, 8:4:6, 8:4:7, 8:4:8, 8:4:9, 8:4:10, 8:5:1, 8:5:2, 8:5:3, 8:5:4, 8:5:5, 8:5:6, 8:5:7, 8:5:8, 8:5:9, 8:5:10, 8:6:1, 8:6:2, 8:6:3, 8:6:4, 8:6:5, 8:6:6, 8:6:7, 8:6:8, 8:6:9, 8:6:10, 8:7:1, 8:7:2, 8:7:3, 8:7:4, 8:7:5, 8:7:6, 8:7:7, 8:7:8, 8:7:9, 8:7:10, 8:8:1, 8:8:2, 8:8:3, 8:8:4, 8:8:5, 8:8:6, 8:8:7, 8:8:8, 8:8:9, 8:8:10, 8:9:1, 8:9:2, 8:9:3, 8:9:4, 8:9:5, 8:9:6, 8:9:7, 8:9:8, 8:9:9, 8:9:10, 8:10:1, 8:10:2, 8:10:3, 8:10:4, 8:10:5, 8:10:6, 8:10:7, 8:10:8, 8:10:9, 8:10:10, 9:1:1, 9:1:2, 9:1:3, 9:1:4, 9:1:5, 9:1:6, 9:1:7, 9:1:8, 9:1:9, 9:1:10, 9:2:1, 9:2:2, 9:2:3, 9:2:4, 9:2:5, 9:2:6, 9:2:7, 9:2:8, 9:2:9, 9:2:10, 9:3:1, 9:3:2, 9:3:3, 9:3:4, 9:3:5, 9:3:6, 9:3:7, 9:3:8, 9:3:9, 9:3:10, 9:4:1, 9:4:2, 9:4:3, 9:4:4, 9:4:5, 9:4:6, 9:4:7, 9:4:8, 9:4:9, 9:4:10, 9:5:1, 9:5:2, 9:5:3, 9:5:4, 9:5:5, 9:5:6, 9:5:7, 9:5:8, 9:5:9, 9:5:10, 9:6:1, 9:6:2, 9:6:3, 9:6:4, 9:6:5, 9:6:6, 9:6:7, 9:6:8, 9:6:9, 9:6:10, 9:7:1, 9:7:2, 9:7:3, 9:7:4, 9:7:5, 9:7:6, 9:7:7, 9:7:8, 9:7:9, 9:7:10, 9:8:1, 9:8:2, 9:8:3, 9:8:4, 9:8:5, 9:8:6, 9:8:7, 9:8:8, 9:8:9, 9:8:10, 9:9:1, 9:9:2, 9:9:3, 9:9:4, 9:9:5, 9:9:6, 9:9:7, 9:9:8, 9:9:9, 9:9:10, 9:10:1, 9:10:2, 9:10:3, 9:10:4, 9:10:5, 9:10:6, 9:10:7, 9:10:8, 9:10:9, 9:10:10, 10:1:1, 10:1:2, 10:1:3, 10:1:4, 10:1:5, 10:1:6, 10:1:7, 10:1:8, 10:1:9, 10:1:10, 10:2:1, 10:2:2, 10:2:3, 10:2:4, 10:2:5, 10:2:6, 10:2:7, 10:2:8, 10:2:9, 10:2:10, 10:3:1, 10:3:2, 10:3:3, 10:3:4, 10:3:5, 10:3:6, 10:3:7, 10:3:8, 10:3:9, 10:3:10, 10:4:1, 10:4:2, 10:4:3, 10:4:4, 10:4:5, 10:4:6, 10:4:7, 10:4:8, 10:4:9, 10:4:10, 10:5:1, 10:5:2, 10:5:3, 10:5:4, 10:5:5, 10:5:6, 10:5:7, 10:5:8, 10:5:9, 10:5:10, 10:6:1, 10:6:2, 10:6:3, 10:6:4, 10:6:5, 10:6:6, 10:6:7, 10:6:8, 10:6:9, 10:6:10, 10:7:1, 10:7:2, 10:7:3, 10:7:4, 10:7:5, 10:7:

6, 10:7:7, 10:7:8, 10:7:9, 10:7:10, 10:8:1, 10:8:2, 10:8:3, 10:8:4, 10:8:5, 10:8:6, 10:8:7, 10:8:8, 10:8:9, 10:8:10, 10:9:1, 10:9:2, 10:9:3, 10:9:4, 10:9:5, 10:9:6, 10:9:7, 10:9:8, 10:9:9, 10:9:10, 10:10:1, 10:10:2, 10:10:3, 10:10:4, 10:10:5, 10:10:6, 10:10:7, 10:10:8, 10:10:9, or any ratio in between. In a composition comprising a first sleep-inducing agonist, a second sleep-inducing agonist, a third sleep-inducing agonist, and a combination of a sleep-inducing antagonist and a gallic acid ester, the synergistic ratio of the amount of the first sleep-inducing agonist to the amount of the second sleep-inducing agonist to the amount of the third sleep-inducing agonist to the combined amount of the sleep-inducing antagonist and the gallic acid ester may be about 1:1:1:1, 1:1:1:2, 1:1:1:3, 1:1:1:4, 1:1:1:5, 1:1:1:6, 1:1:1:7, 1:1:1:8, 1:1:1:9, 1:1:1:10, 1:2:1:1, 1:2:1:2, 1:2:2:1, 1:2:3:1, 1:2:3:1.59, 1:2:3:2, 1:2:3:3, 1:2:3:4, 1:2:3:4.125, 1:2:3:5, 1:2:3:6, 1:2:3:7, 1:2:3:8, 1:2:3:9, 1:2:3:10, 1:3:1:1, 1:3:2:1, 1:3:3:1, 1:3:4:1, 1:3:5:1, 1:3:6:1, 1:3:7:1, 1:3:8:1, 1:3:9:1, 1:3:10:1, 1:2:4:1, 1:2:4:2, 1:2:4:3, 1:2:4:4, 1:2:4:5, 1:2:4:6, 1:2:4:7, 1:2:4:8, 1:2:4:9, 1:2:4:10, 1:3:1:1, 1:3:2:1, 1:3:3:1, 1:3:3:2, or any ratio in between. The synergistic ratio is not particularly limited. In view of the results and discussion contained herein, one of skill in the art would understand how to formulate a composition, as described herein, to achieve the results described herein.

In certain embodiments, the composition may also comprise a brain-health supporting agent. An example of the brain-health supporting agent is phosphatidyl serine. The amount of the brain-health supporting agent may be about 10 µg, 15 µg, 20 µg, 25 µg, 30 µg, 35 µg, 40 µg, 45 µg, 50 µg, 55 µg, 60 µg, 65 µg, 70 µg, 75 µg, 80 µg, 85 µg, 90 µg, 95 µg, 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or any amount therebetween. The amount of each sleep-inducing agonist and the amount of a brain-health supporting agent are present in a synergistic ratio. For example, a composition may comprise a synergistic ratio of 1:2:3:1 of a first sleep-inducing agonist to a second sleep-inducing agonist to a third agonist to a brain-health supporting agent. The amount of each sleep-inducing agonist, the amount of a combination of a sleep-inducing antagonist and a gallic acid ester, and the amount of a brain-health supporting agent are also present in a synergistic ratio. For example, in a composition comprising a first sleep-inducing agonist, a second sleep-inducing agonist, a combination of a sleep-inducing antagonist and a gallic acid ester, and a brain-health supporting agent, the synergistic ratio may be about 1:2:4.12:1 of the first sleep-inducing agonist to the second sleep-inducing agonist to the combination of a sleep-inducing antagonist and a gallic acid ester to the brain-health supporting agent. In view of the results and discussion contained herein, one of skill in the art would understand how to formulate a composition of the instant disclosure to achieve the results described herein.

In some embodiments, a composition, as described herein, may comprise a pharmaceutically acceptable vehicle, carrier, or diluent.

The compositions described herein can be used to improve and/or maintain healthy sleep quality. In some embodiments, the composition as described herein can be used to reduce sleep latency and support and/or maintain a healthy sleep cycle. In some embodiments, the compositions can be used to promote deep sleep. In some embodiments, the compositions can be used to increase memory consolidation and muscle recovery.

In some embodiments, a composition described herein is administered to a subject to promote healthy sleep quality. In some embodiments, a composition is administered to a subject to improve next-day cognitive function. In certain embodiments, a composition, as described herein, is administered to a subject to treat, ameliorate, prevent, or reduce one or more symptoms associated with menopause. Examples of the one or more symptoms are sleep difficulty and loss of memory and/or concentration.

In certain embodiments, a composition described herein is administered to a subject who cannot fall into sleep due to caffeine to promote sleep. For example, a composition described herein can be administered to a subject who takes caffeine-heavy pre-workout supplements in the evening before bed to induce sleep and thus maintain a healthy sleep cycle. A composition described herein can be administered to a subject prior to, simultaneously with, or after consuming caffeine-containing drinks, foods, and/or supplements.

In certain embodiments, a composition may be formulated as a single dosage form to be administered to a subject orally, buccally, sublingually, or like. For oral administration, each composition disclosed herein can be provided as a tablet, aqueous or oil suspension, dispersible powder or granule, emulsion, hard or soft capsule, syrup, elixir, or beverage. Solid dosage forms such as tablets and capsules may comprise an enteric coating. Compositions intended for oral use can be prepared according to any method known in the art for the manufacture of pharmaceutically acceptable compositions and such compositions may include one or more of the following agents: sweeteners, flavoring agents, coloring agents, coatings, and preservatives. The sweetening and flavoring agents will increase the palatability of the preparation. Tablets containing the complexes in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin, or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

In certain embodiments, a composition described herein can be formulated as separate dosage forms intended to deliver one or more ingredients separately in the composition. For example, (i) each sleep-inducing agonist can be formulated as a separate dosage form; (ii) two sleep-inducing agonists can be formulated as a single dosage form and the other sleep-inducing agonist(s) in the composition can be formulated as a single dosage form that is separated from the-two-sleep-inducing-agonists dosage form; (iii) each sleep-inducing agonist and a sleep-inducing antagonist can be formulated as a separate dosage form; (iv) sleep-inducing agonists can be formulated as a single dosage form and a sleep-inducing antagonist can be formulated as a single dosage form that is separated from the sleep-inducing-agonists dosage form; and (v) sleep-inducing agonists can be formulated as a single dosage form and a sleep-inducing antagonist and a gallic acid ester can be formulated a single dosage form that is separated from the sleep-inducing-agonists dosage form.

By formulating separate dosage forms, a scheduled delivery scheme may be employed. In certain embodiments, a scheduled delivery scheme may provide each sleep-inducing agonist concurrently to a subject. In some embodiments, a scheduled delivery scheme may provide each sleep-inducing agonist and a sleep-inducing antagonist concurrently to a subject. In certain embodiments, a scheduled delivery scheme may provide each sleep-inducing agonist, a sleep-inducing antagonist, and a gallic acid ester concurrently to a subject. In certain embodiments, a scheduled delivery scheme may provide each ingredient in a composition at different times, different frequency, and/or by different delivery routes or forms. Neither the route of administration nor the particular dosage form utilized to achieve such are particularly limited and may be any route of administration or dosage form contemplated herein.

Formulations for oral use can also be presented as hard gelatin-containing or non-gelatinous capsules wherein the active ingredient is mixed with an inert solid diluent, for example calcium carbonate, calcium phosphate or kaolin, or as soft gelatin capsules wherein the active ingredient is mixed with water or an oil medium, such as peanut oil, liquid paraffin, or olive oil. Aqueous suspensions can contain the complex of the described herein admixed with excipients suitable for the manufacture of aqueous suspensions. Such excipients include suspending agents, dispersing, or wetting agents, one or more preservatives, one or more coloring agents, one or more flavoring agents and one or more sweetening agents such as sucrose or saccharin.

Oil suspensions can be formulated by suspending the active ingredient in a vegetable oil, such as *arachis* oil, olive oil, sesame oil or coconut oil, or in a mineral oil such as liquid paraffin. The oil suspension can contain a thickening agent, such as beeswax, hard paraffin or acetyl alcohol. Sweetening agents, such as those set forth above, and flavoring agents can be added to provide a palatable oral preparation. These compositions can be preserved by an added antioxidant such as ascorbic acid. Dispersible powders and granules suitable for preparation of an aqueous suspension by the addition of water can provide the active ingredient in admixture with a dispersing or wetting agent, a suspending agent, and one or more preservatives. Additional excipients, for example sweetening, flavoring, and coloring agents, can also be present.

Syrups and elixirs can be formulated with sweetening agents, such as glycerol, sorbitol, or sucrose. Such formulations can also contain a demulcent, a preservative, a flavoring, or a coloring agent.

Utilization of controlled release vehicles would readily be envisaged by those of skill in the pharmaceutical sciences in view of the disclosure contained herein, and these aspects can be applied to nutritional and dietary supplements. The technology and products in this art are variably referred to as controlled release, sustained release, prolonged action, depot, repository, delayed action, retarded release, and timed release; the words "controlled release" as used herein is intended to incorporate each of the foregoing technologies.

Numerous controlled release vehicles can be used, including biodegradable or bio-erodible polymers such as polylactic acid, polyglycolic acid, and regenerated collagen. Controlled release drug delivery devices can include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, and can be used in the disclosed methods.

Controlled release preparations can be achieved by the use of polymers to form complexes with or absorb a composition as set forth herein. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of active complex.

Controlled release of active complexes can be taken to mean any of the extended-release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein a composition as disclosed herein is dissolved in an aqueous constituent to gradually release over time, can be prepared by copolymerization of hydrophilic mono-olefinic monomers such as ethylene glycol methacrylate. Matrix devices, wherein a composition is dispersed in a matrix of carrier material, can be used. The carrier can be porous, non-porous, solid, semi-solid, permeable, or impermeable. Alternatively, a device comprising a central reservoir of a composition disclosed herein surrounded by a rate controlling membrane can be used to control the release of the complex. Rate controlling membranes include ethylene-vinyl acetate copolymer or butylene terephthalate/polytetramethylene ether terephthalate. Use of silicon rubber or ethylene-vinyl alcohol depots are also contemplated.

Controlled release oral formulations can also be used. In an embodiment, a composition as described herein is incorporated into a soluble or erodible matrix, such as a pill or a lozenge. In another example, the oral formulations can be a liquid used for sublingual administration. These liquid compositions can also be in the form a gel or a paste. Hydrophilic gums, such as hydroxymethylcellulose, are commonly used. A lubricating agent such as magnesium stearate, stearic acid, or calcium stearate can be used to aid in the tableting process.

In some embodiments, a composition comprising two or more sleep-inducing agonists or comprising a combination of a sleep-inducing antagonist and two or more sleep-inducing agonists described herein is administered orally between 15 minutes and 2 hours before bed. For example, the composition can be administered 15 minutes, 30 minutes, 45 minutes, one hour, one and half hours, 2 hours or any time therebetween before bed. The total amount of agonists or a combination of agonists and an antagonist can be about 10 μg to about 10 g. For example, the amount can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 410 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850 μg, 875 μg, 900 μg, 925 μg, 950 μg, 975 μg, 1000 μg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or amount therebetween.

In some embodiments, a morning blend comprising a sleep-inducing antagonist is administered orally to a subject in the morning first followed by an oral administration of a composition comprising two or more sleep-inducing agonists as described herein between 15 minutes and 2 hours before bed. For example, the two or more sleep-inducing agonists can be administered 15 minutes, 30 minutes, 45 minutes, one hour, one and half hours, two hours, or any time therebetween before bed. The morning blend may comprise caffeine and herbs/substances associated with mental alertness, such as taurine, *Panax ginseng* root extract, L-carnitine, L-tartrate, guarana seed extract, quercetin, branched chain amino acids, *Ginkgo biloba*, milk thistle, inositol, acai berry, yerba mate, glucuronolactone, vitamin A, B vitamins, vitamin C, vitamin E, selenium, and the like, or any combination thereof. The morning blend not only promotes focus and cognitive function during daytime, but also enhances the effects of sleep-inducing agonists and thus promotes deep sleep.

The amount of a sleep-inducing antagonist in the morning blend can be about 10 μg to about 10 g, preferably once per day. For example, the amount can be about 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400μg, 410μ, 425μ, 450μ, 475μ, 500μ, 525μ, 575μ, 600μ, 625μ, 650μ, 675μ g, 700 μg, 725 μg, 750 μg, 775 μg, 800 μg, 825 μg, 850 μg, 875 μg, 900 μg, 925 μg, 950 μg, 975 μg, 1000 μg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or amount therebetween. The total amount of sleep-inducing agonists taken before bed can be about 10 μg to about 10 g. For example, the amount can be 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 125 μg, 150 μg, 175 μg, 200 μg, 225 μg, 250 μg, 275 μg, 300 μg, 325 μg, 350 μg, 375 μg, 400 μg, 410 μg, 425 μg, 450 μg, 475 μg, 500 μg, 525 μg, 575 μg, 600 μg, 625 μg, 650 μg, 675 μg, 700 μg, 725 μg, 750 μg, 775 μg, 800 μg, 825 μg, 850μ, 875μ, 900μ, 925μ, 950μ, 975μ, 1000μ, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, or more, or amount therebetween.

In certain embodiments, compositions can be administered on a daily basis, every two days, every three days, every four days, every five days, every six days, every week, every eight days, every nine days, every ten days, every two weeks, every month, or more or less frequently, as needed to achieve the desired therapeutic effect.

The composition can be suitably administered to a subject at one time or over a series of treatments and may be administered to a subject at any time from diagnosis onwards. The composition may be administered as the sole treatment or in conjunction with other drugs or therapies useful in treating the condition in question.

As used herein, the terms "prevent" and "preventing" can refer to treating a subject who does not yet exhibit symptoms of a disease or condition, but who is susceptible to, or otherwise at risk of, a particular disease or condition, whereby the treatment reduces the likelihood that the patient will develop the disease or condition. As used herein, the terms "treating", "treatment", and the like are used herein to generally refer to obtaining a desired pharmacological and physiological effect and can also refer to a nutritional or nutraceutical effect, the scopes, and meanings of which will be clear to the skilled artisan based upon the context in which these terms are used. The effect may be prophylactic in terms of preventing or partially preventing a disease, symptom, or condition thereof and/or may be therapeutic in terms of a partial or complete cure of a disease, condition, symptom, or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; or (c) relieving the disease, causing regression of the disease and/or its symptoms, conditions, and co-morbidities. In some embodiments, a composition, as described herein, may be administered to maintain healthy levels of a certain condition or biomarker in a subject, such as for example maintaining a healthy level of sleep duration and/or sleep quality. As set forth herein, any composition that is administered to prevent, treat, alleviate, or ameliorate any condition, can also be administered to maintain a healthy level of a physiological or biological condition. In certain embodiments, a composition is administered to maintain a healthy level of one or more of the conditions disclosed herein. The scope and meaning of "preventing," "treating," "treatment," "alleviating," "ameliorating," and "maintaining healthy levels of" would be immediately envisaged by the skilled artisan when viewing the term in the context of the disclosure and the claims. The term "pharmaceutical formulation", "formulation", "composition" and the like can refer to preparations which are in such a form as to permit the biological activity of the active ingredients to be effective, and therefore may be administered to a subject for therapeutic use along with dietary and/or nutritional supplement use. The meaning of these terms will be clear to the skilled artisan based upon the context in which they are used.

As provided herein, the disclosure of a "ratio" of compounds and compositions corresponds to a ratio provided in terms of mass of the components present in the ratio.

As used herein, the term "excipient material" refers to any compound that is part of a formulation that is not an active ingredient, i.e., one that has no relevant biological activity, and which is added to the formulation to provide specific characteristics to the dosage form, including by way of example, providing protection to the active ingredient from chemical degradation, facilitating release of a tablet or caplet from equipment in which it is formed, and so forth.

As used herein, the term "subject" refers to beings that can be treated using the compositions described herein, including human children with attention-deficit/hyperactivity disorder (ADHD) and human adults.

As used herein, the terms "ingredient" and "ingredients" refer to active ingredient(s), including but not limited to each sleep-inducing agonist, a sleep-inducing antagonist, a gallic acid ester, and a brain-supporting agent described herein.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

EXAMPLES

Deep sleep offers specific physical and mental benefits and is an indicator of healthy sleep quality. Agonists of GABAA receptors, GABAB receptor 1, GABAB receptor 2, GluA1 receptor, GluN1 receptor, GluN2A receptor, and/or 5-HTA1 induce deep sleep. Deep sleep can be indicated by long sleep duration, short sleep latency, high electroencephalography (EEG) amplitude, and/or low EEG frequency.

Example 1

A preclinical study was performed to evaluate the efficacy of six exemplary compositions (see Table 1 below) by measuring GABAA receptor 2, GABAB receptor 1, GABAB receptor 2, GluA1, GluN1, GluN2A, 5-HTA1, EEG amplitude, EEG frequency, sleep duration, and sleep latency.

Five male BALB/c mice per treatment arm (age: 8 weeks; weight: 180±20 g) were housed in a controlled environment with a 12:12-h light-dark cycle at 22° C. and were provided with mice chow and water ad libitum. The mice were fasted for 24 hours prior to the study, which was conducted between 1 μm and 5 μm and under the National Institutes of Health's Guidelines for the Care and Use of Laboratory Animals and approved by the Ethics Committee of the Medipol University. The mice were divided into eight groups and anesthetized with urethane (1.25 g/kg, i.p.; Sigma U2500) and carefully placed in a stereotaxic frame. Rectal temperatures were maintained between 36.5° C. and 37.0° C. using a feedback-controlled-heating system (507221F, Harvard Apparatus, ABD). Lidocaine (2.0%) was applied on the incision area to prevent any occurrence of pain. A midline incision was made on the skin along the sagittal suture of the skull. A part of the cranium overlying the left parietal cortex was removed using a dental drill. Ag—AgCl ball electrodes were placed on the left somatomotor cortex (1 mm anterior/1.5 mm lateral from bregma; 3 mm posterior/1.5 mm lateral from bregma) and the reference electrode was attached to the left foot for an ECoG recording. Group 1 were treated with saline. To induce sleep disturbance, 7.5 mg/kg caffeine was injected intraperitoneally at minute 15 of recordings to groups 2-8. At minute 30, saline and each of the six compositions were respectively injected to groups 2-8. The compositions were dissolved in distilled water and the concentration of each resultant solution was adjusted so that the injection volume was constant at 1.0 ml/kg BW.

After the administration, the mice were placed in individual cages and subjected to measurements of sleep latency and duration. Brain electrical activity were monitored and recorded for a total of 2 hours. Signals were sampled at 1000 Hz with a band-pass filter set at 0.5-500 Hz by using the PowerLab system (16/30, AD Instruments, Castle Hill, Australia). The EEG-frequency and amplitude were determined using LabChart 8.1.17 software (AD Instruments, New South Wales, Australia).

After two hours, the mice were sacrificed under deep anesthesia. Their brains were removed and Western blot analysis was used to determine protein concentrations. 50 μg of protein was electrophoresed on 4-15% Tris-Glycine polyacrylamide gels, transferred to Immobilon-P PVDF membranes, blocked for 1 hour in 5% skim milk, and incubated overnight at 4° C. with GABAA receptor 2, GABAB receptor 1, GABAB receptor 2, GluA1, GluN1, GluN2A, or 5-HTA1. Membranes were then incubated with horseradish peroxidase (HRP) conjugated IgG secondary antibody. Bands were quantified using Image software and normalized to actin as a loading control. Data was analyzed using the GLM procedure of SAS and given as mean±SEM. A sample size of five per treatment was calculated based on a power of 85% and a p-value of 0.05. The treatments were compared using ANOVA and Student's unpaired t-test and P<0.05 was considered statistically significant.

The results are shown in FIGS. 1A-1K.

TABLE 1

| | Combo 1 (HED mg) | Combo 2 (HED mg) | Combo 3 (HED mg) | Combo 4 (HED mg) | Combo 5 (HED mg) | Combo 6 (HED mg) |
| --- | --- | --- | --- | --- | --- | --- |
| Magnesium glycinate | 100 | 100 | 100 | 100 | 100 | 100 |
| L-theanine | 200 | 200 | 200 | 200 | 200 | 200 |
| GABA | 300 | 300 | | | 300 | 300 |
| SAMe + Propyl gallate | | 400 + 12.5 | 400 + 12.5 | 400 + 12.5 | | 400 + 12.5 |
| Phosphatidyl serine | | | | 100 | 100 | 100 |

HED refers to human equivalent dosage.

FIG. 1A shows that, while in mice treated with caffeine, the percentage of GABAA receptor 2 was significantly reduced from 100% to about 25%, in mice treated with Combo 1, Combo 2, Combo 3, Combo 4, Combo 5, and Combo 6, the percentages of GABAA receptor 2 were reduced, respectively, from 100% to about 55%, from 100% to about 75%, from 100% to about 35%, from 100% to about 40%, from 100% to about 60%, and from 100% to about 78%.

Figure 1B:
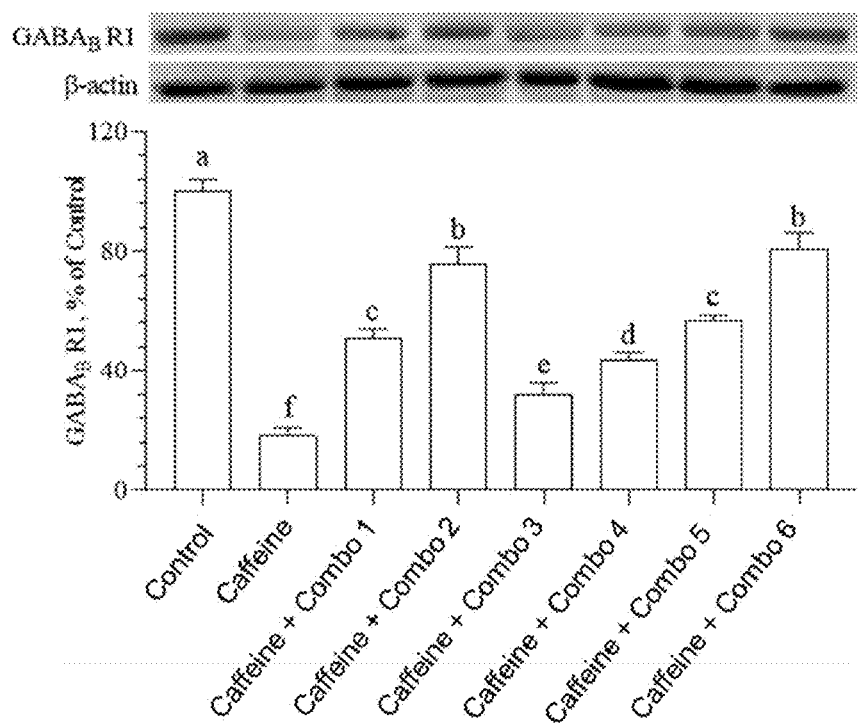
FIG. 1B shows the percentage of GABAB receptor 1 in mice treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1B shows that in mice treated with caffeine, the percentage of GABAB receptor 1 was significantly reduced from 100% to about 18%, as compared to mice treated with Combo 1, Combo 2, Combo 3, Combo 4, Combo 5, and Combo 6, where the percentages of GABAB receptor 1 were reduced, respectively, from 100% to about 50%, from 100% to about 78%, from 100% to about 35%, from 100% to about 42%, from 100% to about 58%, and from 100% to about 80%.

Figure 1C:
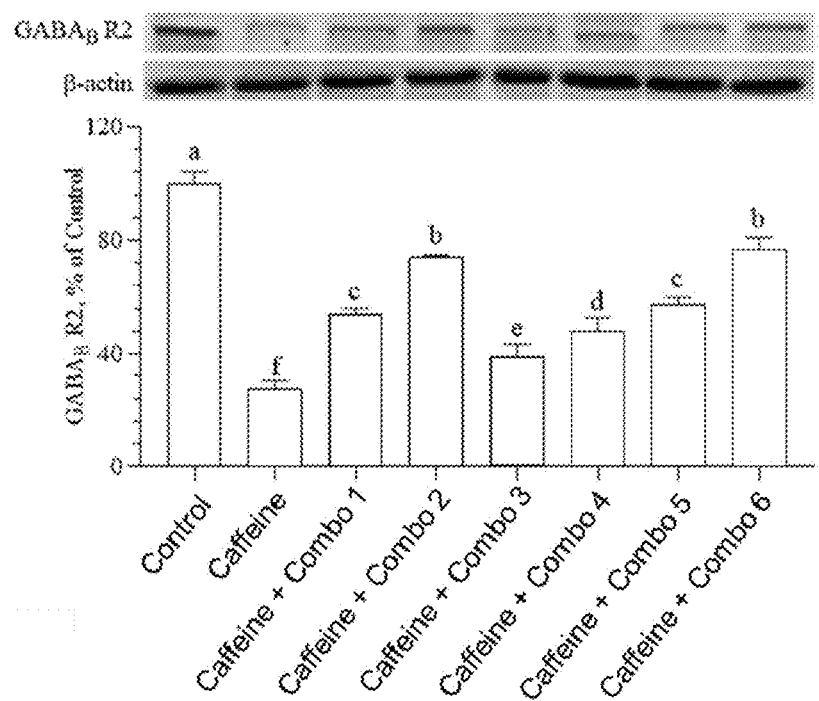
FIG. 1C shows the percentage of GABAB receptor 2 in mice, treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1C shows that in mice treated with caffeine, the percentage of GABAA receptor 2 was significantly reduced from 100% to about 28% and by contrast, in mice treated with Combo 1, Combo 2, Combo 3, Combo 4, Combo 5, and Combo 6, the percentages of GABAA receptor 2 were reduced, respectively, from 100% to about 56%, from 100% to about 75%, from 100% to about 40%, from 100% to about 45%, from 100% to about 58%, and from 100% to about 78%.

Figure 1D:
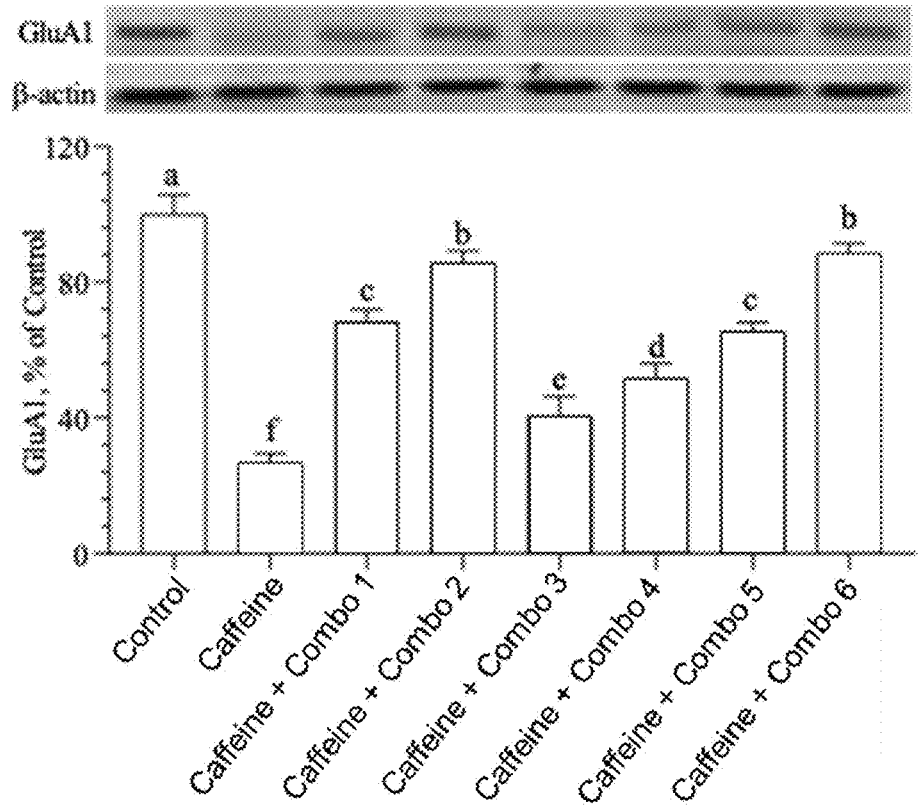
FIG. 1D shows the percentage of GluA1 in mice treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1D shows that in mice treated with caffeine, the percentage of GluA1 receptor was significantly reduced from 100% to about 26% and in mice treated with Combo 1, Combo 2, Combo 3, Combo 4, Combo 5, and Combo 6, the percentages of GluA1 receptor were reduced, respectively, from 100% to about 70%, from 100% to about 82%, from 100% to about 40%, from 100% to about 50%, from 100% to about 65%, and from 100% to about 90%.

Figure 1E:
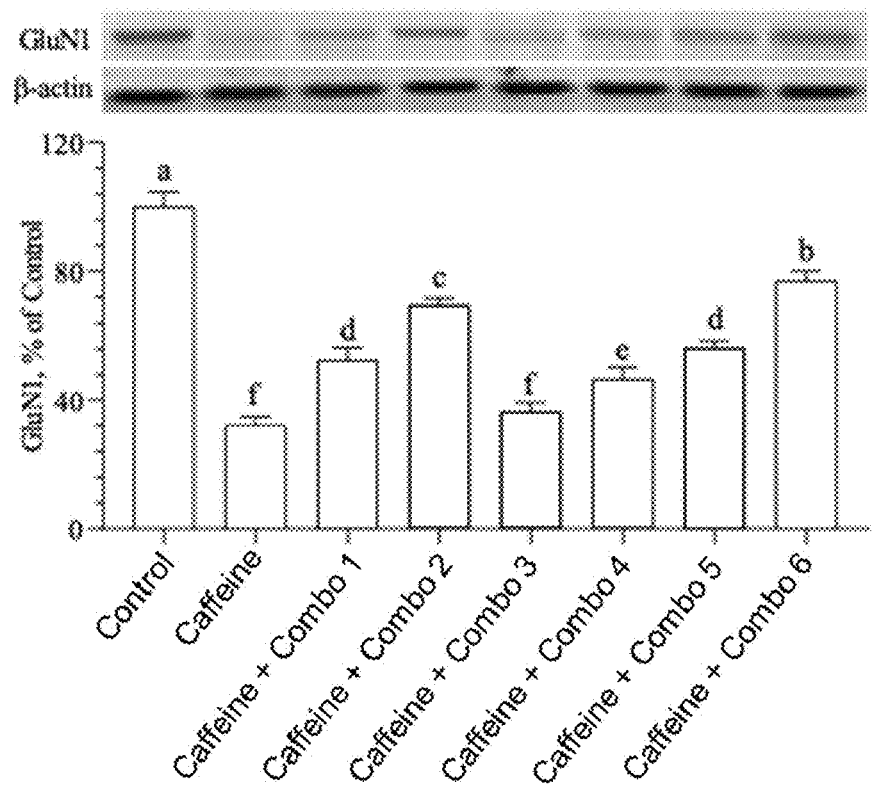
FIG. 1E shows the percentage of GluN1 in mice treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1E shows that while in mice treated with caffeine, the percentage of GluN1 receptor was significantly reduced from 100% to about 35%, in mice treated with Combo 1, Combo 2, Combo 3, Combo 4, Combo 5, and Combo 6, the percentages of GluN1 receptor were reduced, respectively, from 100% to about 55%, from 100% to about 70%, from 100% to about 38%, from 100% to about 45%, from 100% to about 58%, and from 100% to about 78%.

Figure 1F:
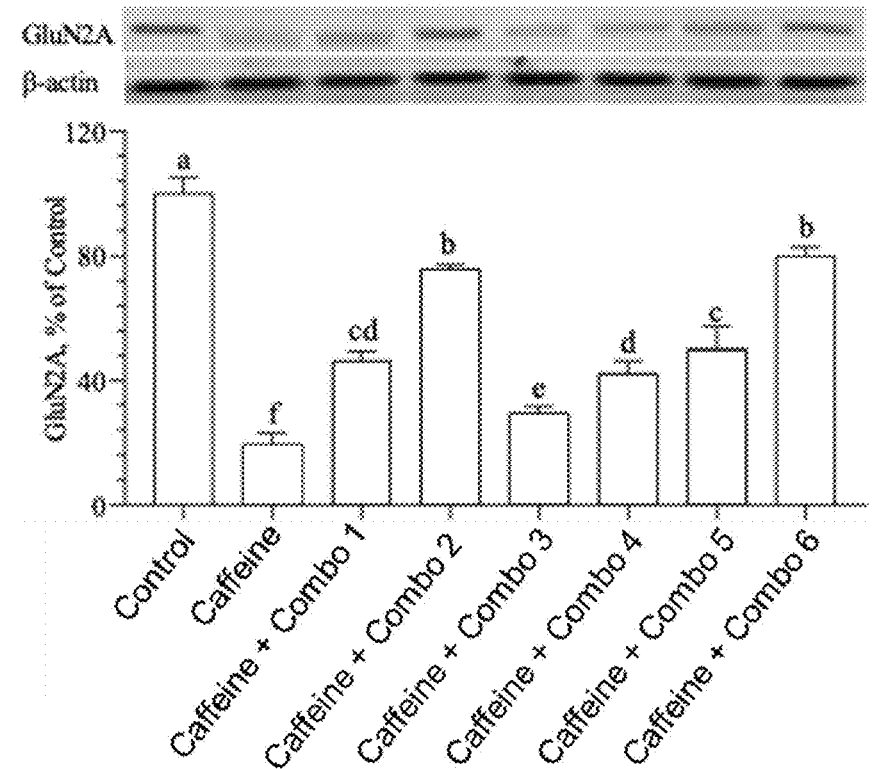
FIG. 1F shows the percentage of GluN2A in mice, treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1F shows that in mice treated with caffeine, the percentage of GluN2A receptor was significantly reduced from 100% to about 20% as compared to mice treated with Combo 1, Combo 2, Combo 3, Combo 4, Combo 5, and Combo 6, where the percentages of GluA1 receptor were reduced, respectively, from 100% to about 45%, from 100% to about 78%, from 100% to about 30%, from 100% to about 42%, from 100% to about 50%, and from 100% to about 80%.

Figure 1G:
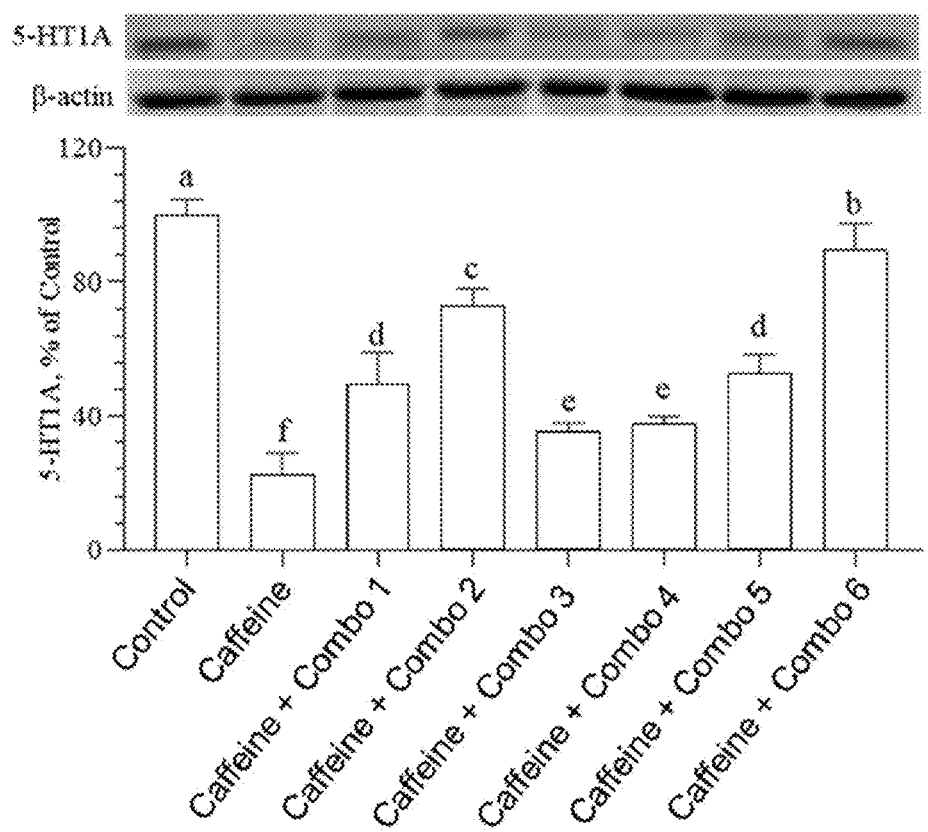
FIG. 1G shows the percentage of 5-HT1A in mice, treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1G shows that in mice treated with caffeine, the percentage of 5-HT1A receptor was significantly reduced from 100% to about 20% as compared to mice treated with Combo 1, Combo 2, Combo 3, Combo 4, Combo 5, and Combo 6, where the percentages of 5-HT1A receptor were reduced, respectively, from 100% to about 50%, from 100% to about 75%, from 100% to about 35%, from 100% to about 40%, from 100% to about 55%, and from 100% to about 90%.

In short, the data shown in FIGS. 1A-1G demonstrates that the compositions described herein can beneficially offset/reverse the effect of caffeine and as such, can induce deep sleep. The compositions described herein provide unexpectedly superior benefits of inducing deep sleep even when a subject ingested or used a stimulant such as caffeine.

Figure 1H:
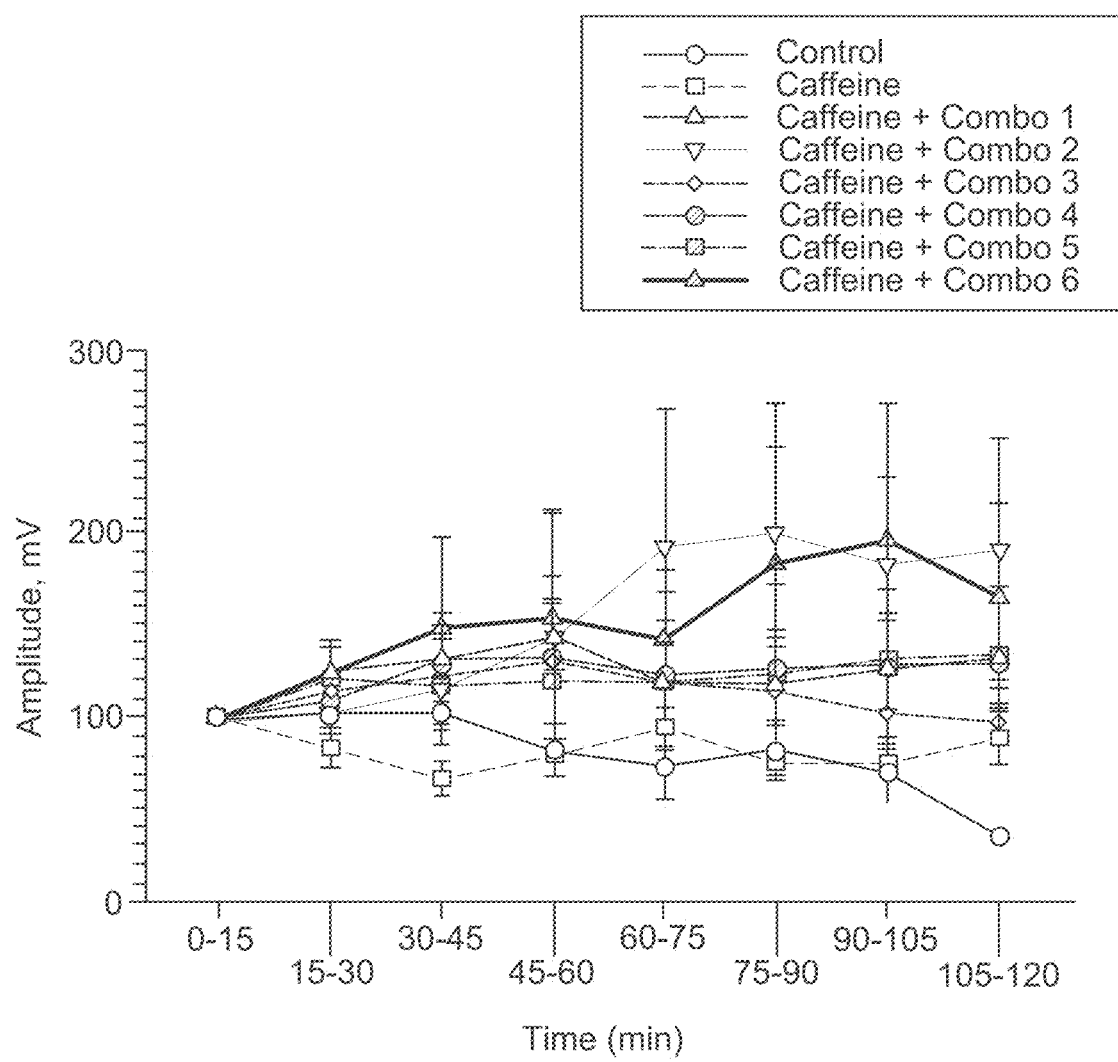
FIG. 1H shows the EEG amplitude in mice treated with caffeine, Combo 1 together with caffeine, Combo 2 together with caffeine, Combo 3 together with caffeine, Combo 4 together with caffeine, Combo 5 together with caffeine, or Combo 6 together with caffeine.
Figure 1I:
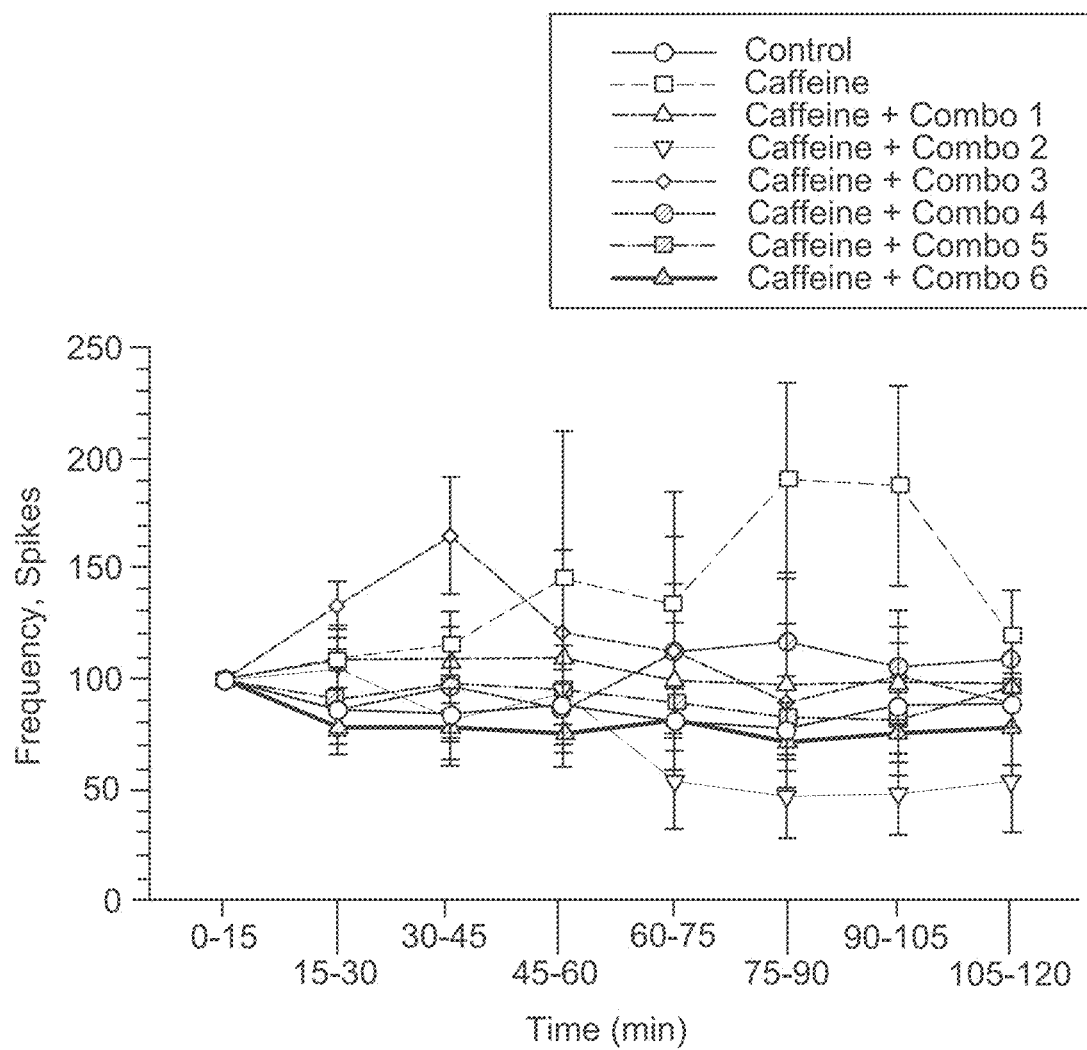
FIG. 1I shows the EEG frequency in mice treated with caffeine, Combo 1 together with caffeine, Combo 2 together with caffeine, Combo 3 together with caffeine, Combo 4 together with caffeine, Combo 5 together with caffeine, or Combo 6 together with caffeine.

FIG. 1H shows that the EEG amplitude in mice treated with caffeine drastically decreased from about 100 mV to about 70 mV within 75 minutes and by contrast, in mice treated with a combination of caffeine and any one of the six exemplary compositions, the EEG amplitudes increased from 100 mV to at least 110 mV. FIG. 1I shows that the EEG frequency in mice treated with caffeine increased significantly from about 100 spikes to about 200 spikes in 90 minutes, significantly different than those in mice treated with a combination of caffeine and any one of the six exemplary compositions, which not only showed no increase as would be expected due to the administration of caffeine, but the spikes actually decreased from about 100 spikes to at least about 90 spikes. These unexpectedly superior results further demonstrate that the compositions described herein offset the effect of caffeine and therefore, can promote deep sleep.

Figure 1J:
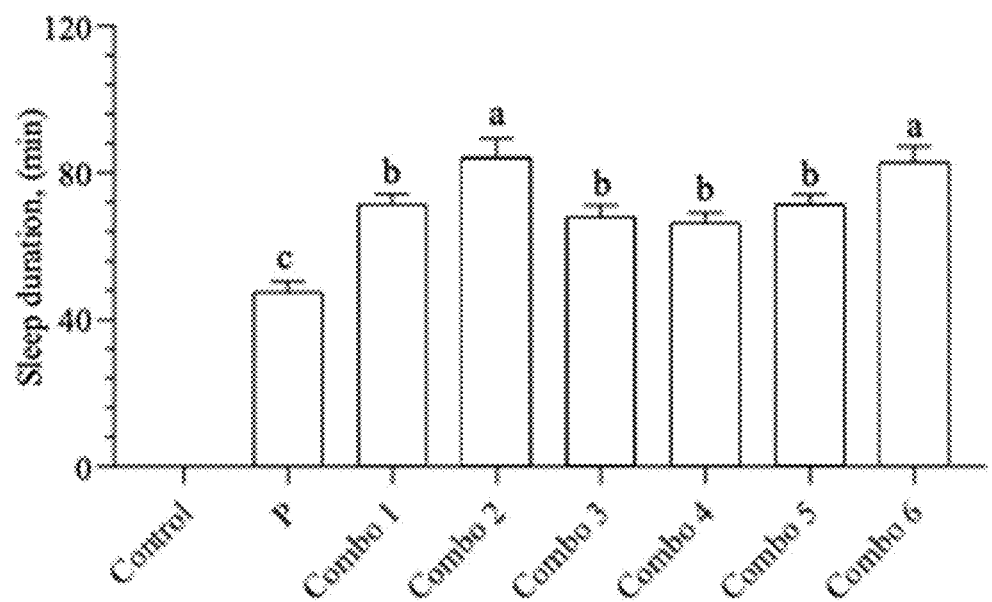
FIG. 1J shows the sleep duration in mice treated with pentobarbital (42 mg/kg), Combo 1 together with caffeine, Combo 2 together with caffeine, Combo 3 together with caffeine, Combo 4 together with caffeine, Combo 5 together with caffeine, or Combo 6 together with caffeine.
Figure 1K:
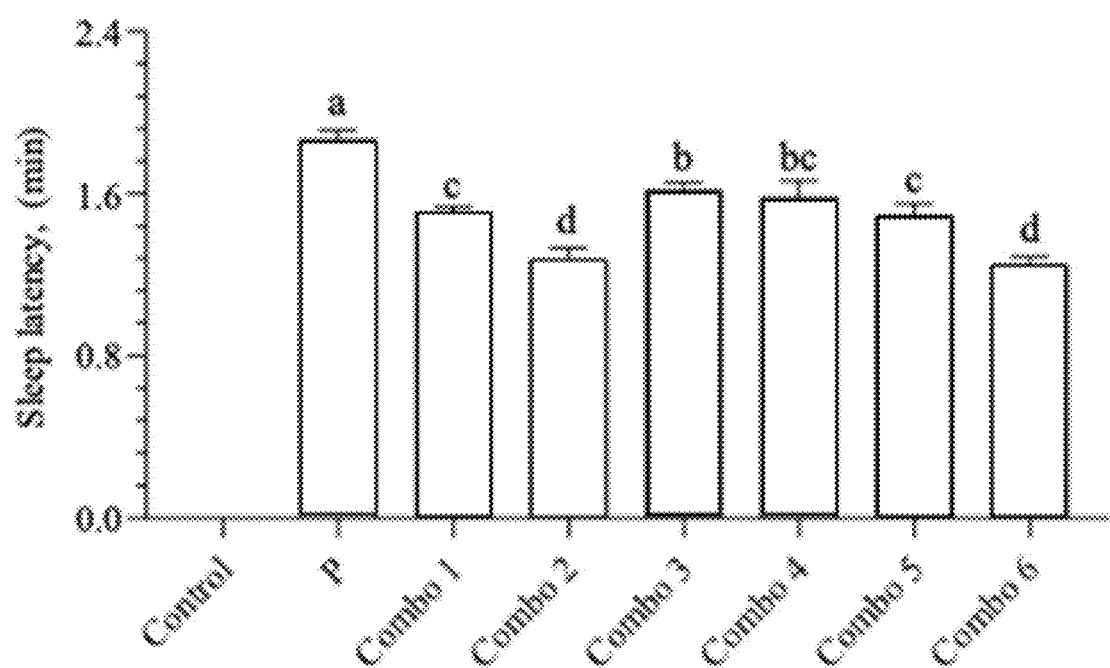
FIG. 1K shows the sleep latency in mice treated with pentobarbital (42 mg/kg), Combo 1 together with caffeine, Combo 2 together with caffeine, Combo 3 together with caffeine, Combo 4 together with caffeine, Combo 5 together with caffeine, or Combo 6 together with caffeine.

FIG. 1J shows the sleep duration in mice treated with any one of the six exemplary compositions ranged from about 70 minutes to about 85 minutes, unexpectedly much longer than that in mice treated with pentobarbital, which was about 50 minutes. FIG. 1K shows that the sleep latency in mice treated with any one of the six exemplary compositions ranged from 1.4 minutes to 1.6 minutes, much shorter than that in mice treated with pentobarbital, which was about 2 minutes. The results indicate that the compositions described herein are unexpectedly superior in increasing sleep duration compared to pentobarbital as pentobarbital is a known-drug for treatment of insomnia.

Example 2

Another preclinical study was conducted to evaluate two exemplary compositions described herein for their effect on deep sleep as compared to magnesium glycinate (a magnesium salt that reduces the excitability of the nervous system), L-theanine (an amino acid that improves sleep quality), GABA (an agent that promotes relaxation), and a combination of SAMe (an agent that increases energy) and propyl gallate (an antioxidant).

Ovariectomized female mice were divided into 8 groups and under treatment for 1-3 weeks. Each day, Group 1 was treated with saline as control; group 2 was treated with 7.5 mg/kg caffeine and saline; group 3 was treated with 7.5 mg/kg caffeine and 100 mg HED of magnesium glycinate; group 4 was treated with 7.5 mg/kg caffeine and 200 mg HED of L-theanine; group 5 was treated with 7.5 mg/kg caffeine and 300 mg HED of GABA; group 6 was treated with 7.5 mg/kg caffeine, 150 mg HED of SAMe, and 9 mg HED of propyl gallate; group 7 was treated with 7.5 mg/kg caffeine, 100 mg HED of magnesium glycinate, 200 mg HED of L-theanine, and 300 mg HED of GABA; and group 8 was treated with 7.5 mg/kg caffeine, 100 mg HED of magnesium glycinate, 200 mg HED of L-theanine, and 300 mg HED of GABA, 150 mg HED of SAMe, and 9 mg HED of propyl gallate. EEG amplitude, EEG frequency, sleep duration, sleep latency, percentages of GABAA receptor 2, percentages of GABAB receptor 1, percentages of GABAB receptor 2, percentages of GluA1, percentages of GluN1, and percentages of GluN2A were measured by the procedures set forth in Examples 1 and 2. Melatonin levels were measured using ELISA kits. The results are shown in FIGS. 2A-2K.

Figure 2A:
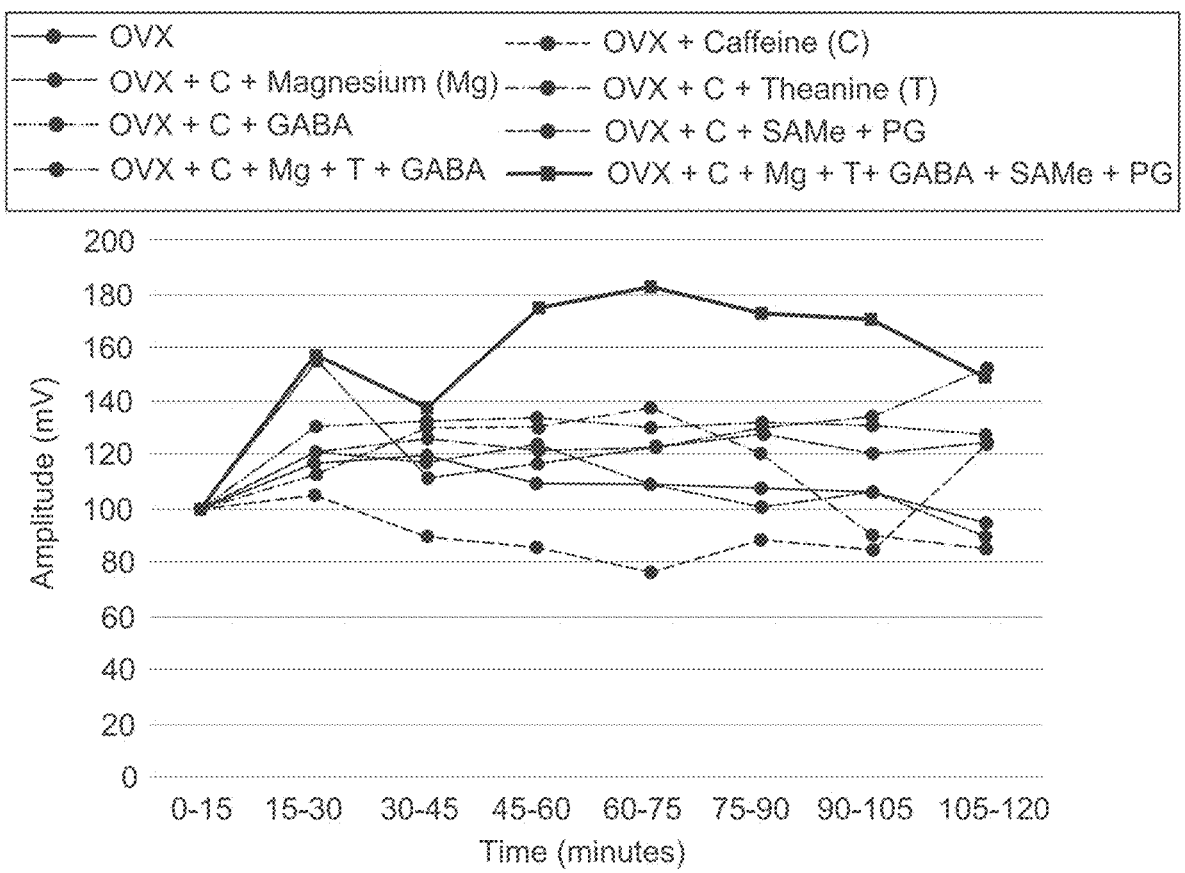
FIG. 2A shows the EEG amplitude in ovariectomized (OVX) female mice treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2A shows that between 45-90 minutes, the EEG amplitude in group 8 was about 180 mV, unexpectedly much higher than groups 1-6, which had EEG amplitudes ranging from about 90 mV to about 130 mV. Furthermore, the EEG amplitude in group 7 was about 135 mV, still higher than that in groups 1-6.

Figure 2B:
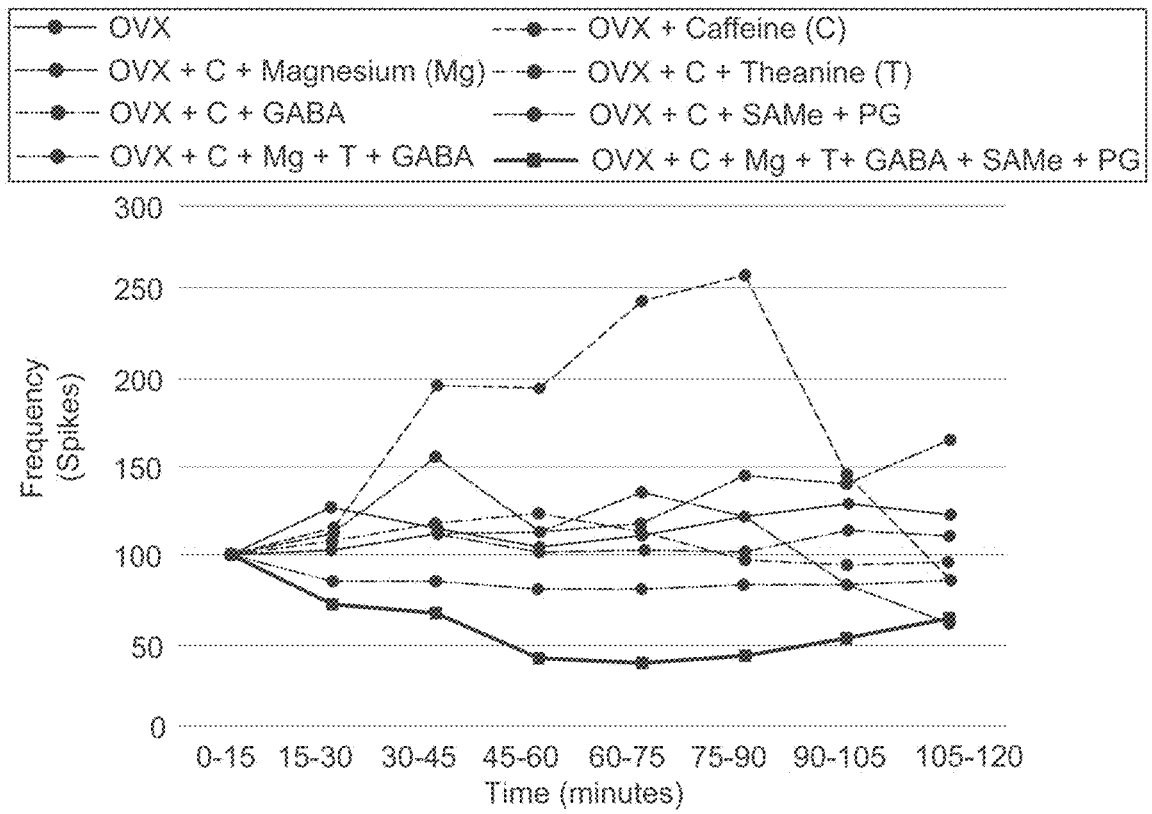
FIG. 2B shows the EEG frequency in OVX female mice treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2B shows that between 45-90 minutes, the EEG frequencies in group 7 and group 8 were respectively about 80 spikes and 50 spikes, unexpectedly much lower than those in groups 1-6, which ranged from 100 to 250 spikes.

Figure 2C:
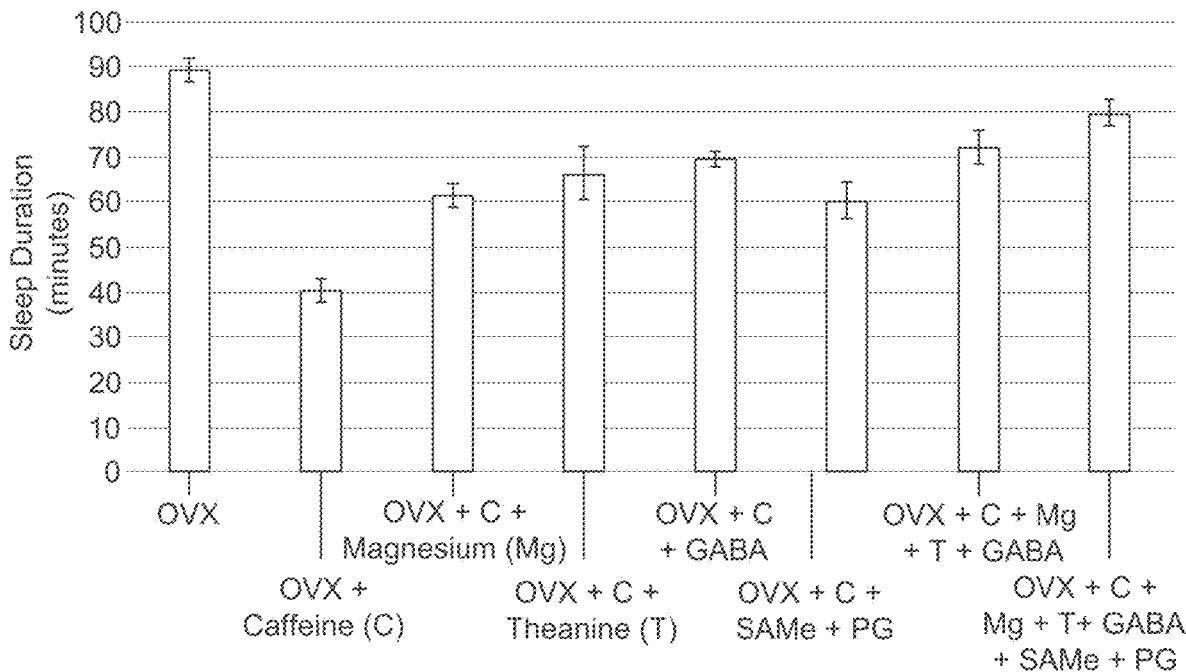
FIG. 2C shows the sleep duration in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2C shows that the sleep durations in groups 7 and 8 were respectively about 72 minutes and 80 minutes, unexpectedly much longer than those in groups 1-6, ranging from 40 minutes to 69 minutes.

Figure 2D:
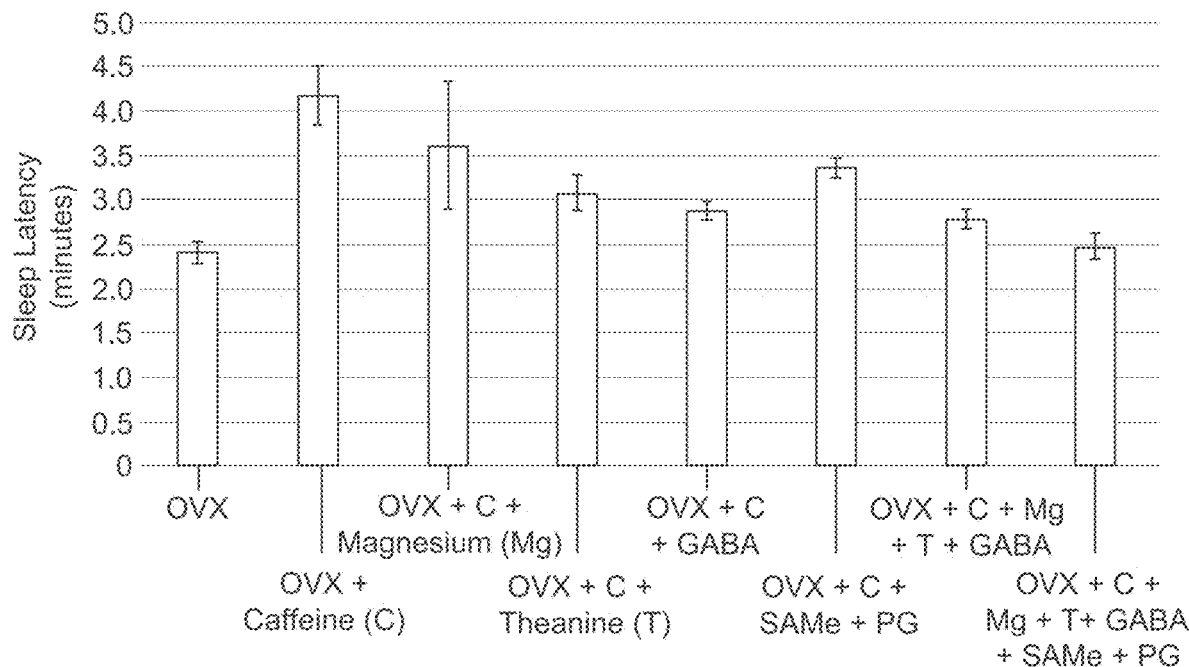
FIG. 2D shows the sleep latency in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2D shows that the sleep latencies in groups 7 and 8 were respectively about 2.6 minutes and about 2.5 minutes, unexpectedly much shorter than those in groups 1-6, ranging from 2.8 minutes to 4.2 minutes.

Figure 2E:
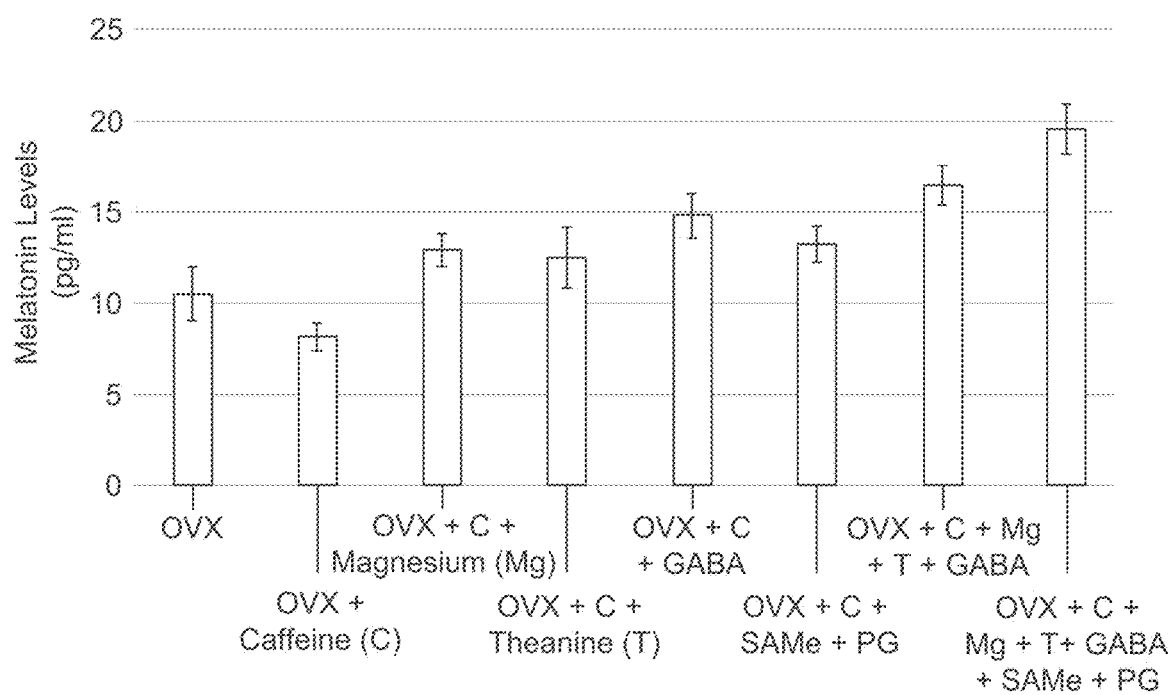
FIG. 2E shows the melatonin level in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2E shows that the melatonin levels in groups 7 and 8 were respectively about 16 μg/ml and about 19 μg/ml, unexpectedly much higher than those in groups 1-6, ranging from about 7 μg/ml to 14 μg/ml.

Figure 2F:
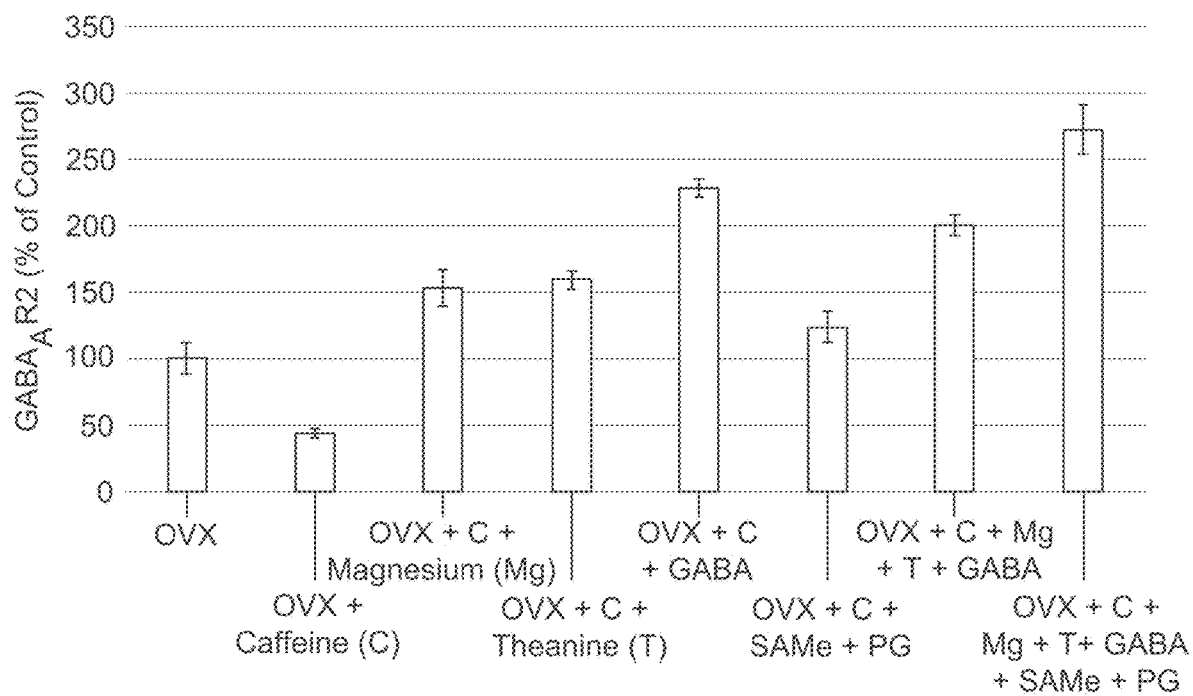
FIG. 2F shows the percentage of GABAA receptor 2 in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2F shows that the percentage of GABAA receptor 2 in group 8 was about 275%, unexpectedly much higher than those in groups 1-6, ranging from about 100% to 225%.

Figure 2G:
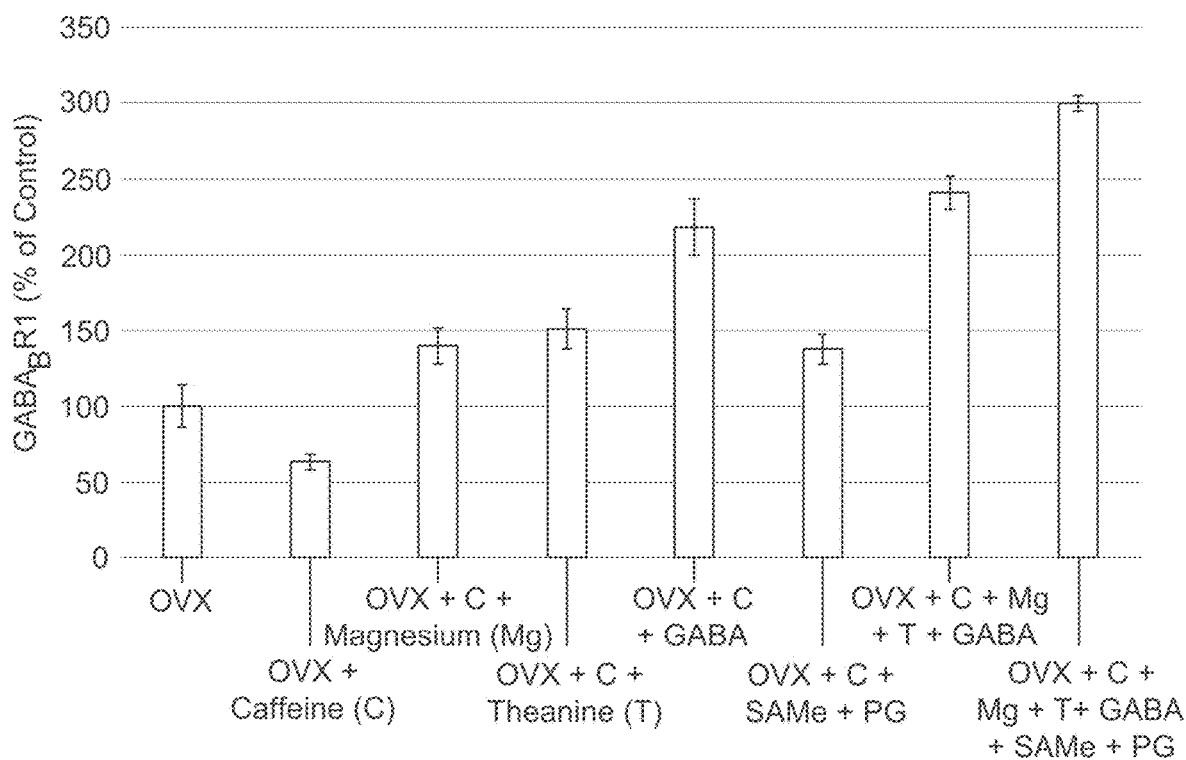
FIG. 2G shows the percentage of GABAB receptor 1 in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2G shows that the percentages of GABAB receptor 1 in groups 7 and 8 were respectively about 240% and 300%, unexpectedly much higher than those in groups 1-6, ranging from about 60% to 210%.

Figure 2H:
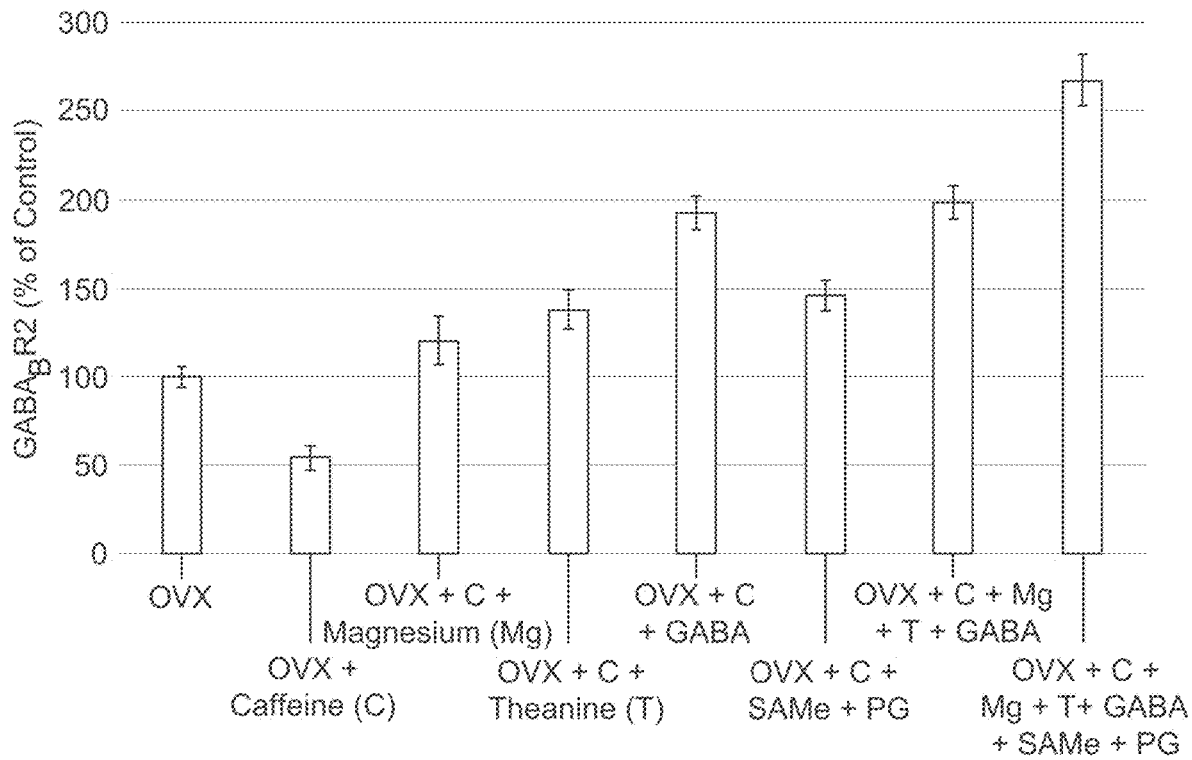
FIG. 2H shows the percentage of GABAB receptor 2 in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2H shows that the percentages of GABAB receptor 2 in groups 7 and 8 were respectively about 200% and 260%, unexpectedly much higher than those in groups 1-6, ranging from about 55% to 180%.

Figure 2I:
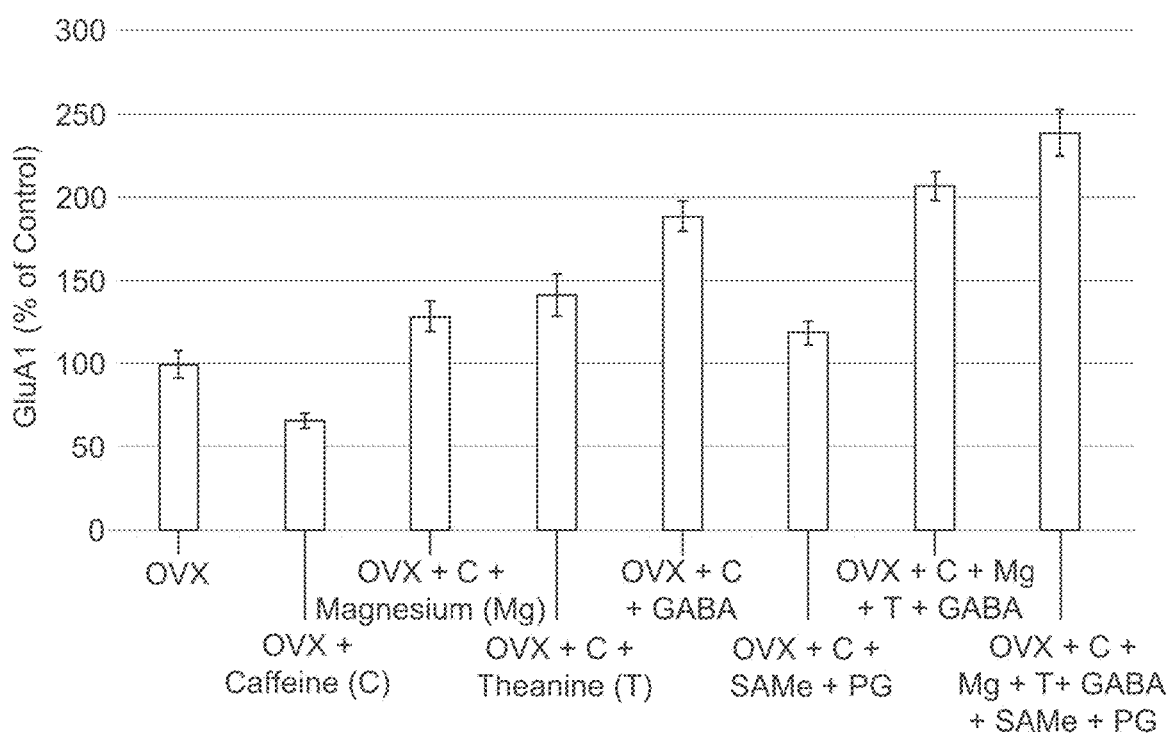
FIG. 2I shows the percentage of GluA1 in OVX female mice, treated with (i) saline (control), (ii) a combination of caffeine and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2I shows that the percentages of GluA1 receptor in groups 7 and 8 were respectively about 210% and 240%, unexpectedly much higher than those in groups 1-6, ranging from about 60% to 180%.

Figure 2J:
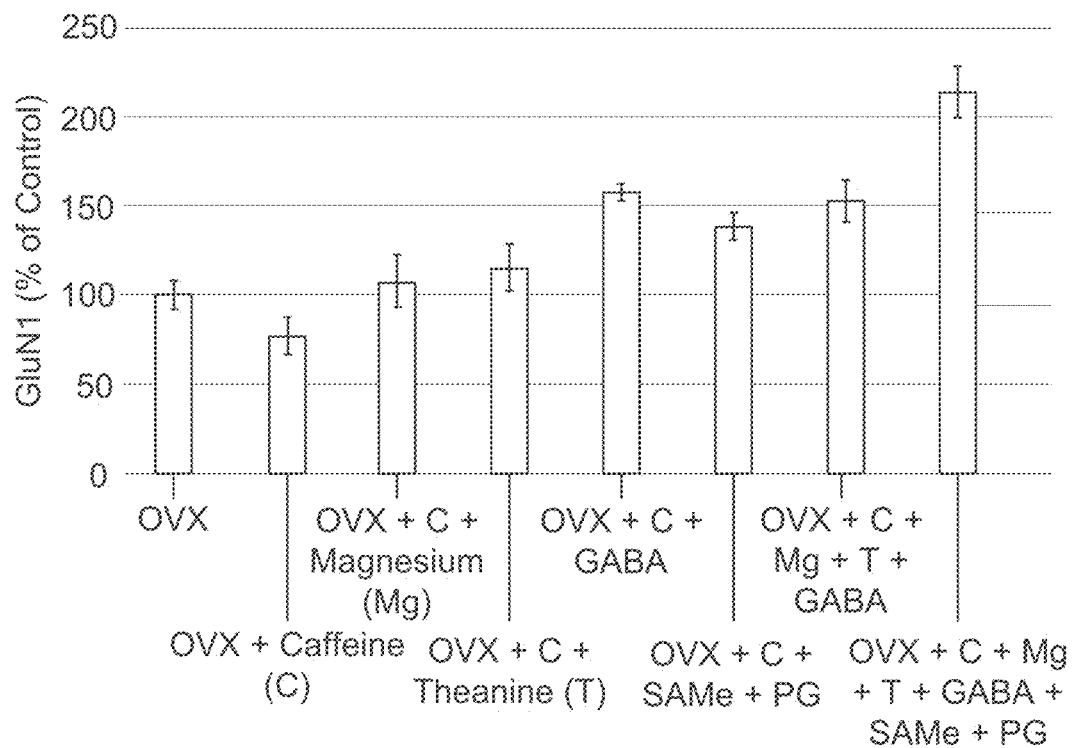
FIG. 2J shows the percentage of GluN1 in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2J shows that the percentage of GluN1 receptor in group 8 was about 220%, unexpectedly much higher than those in groups 1-6, ranging from about 70% to 155%.

Figure 2K:
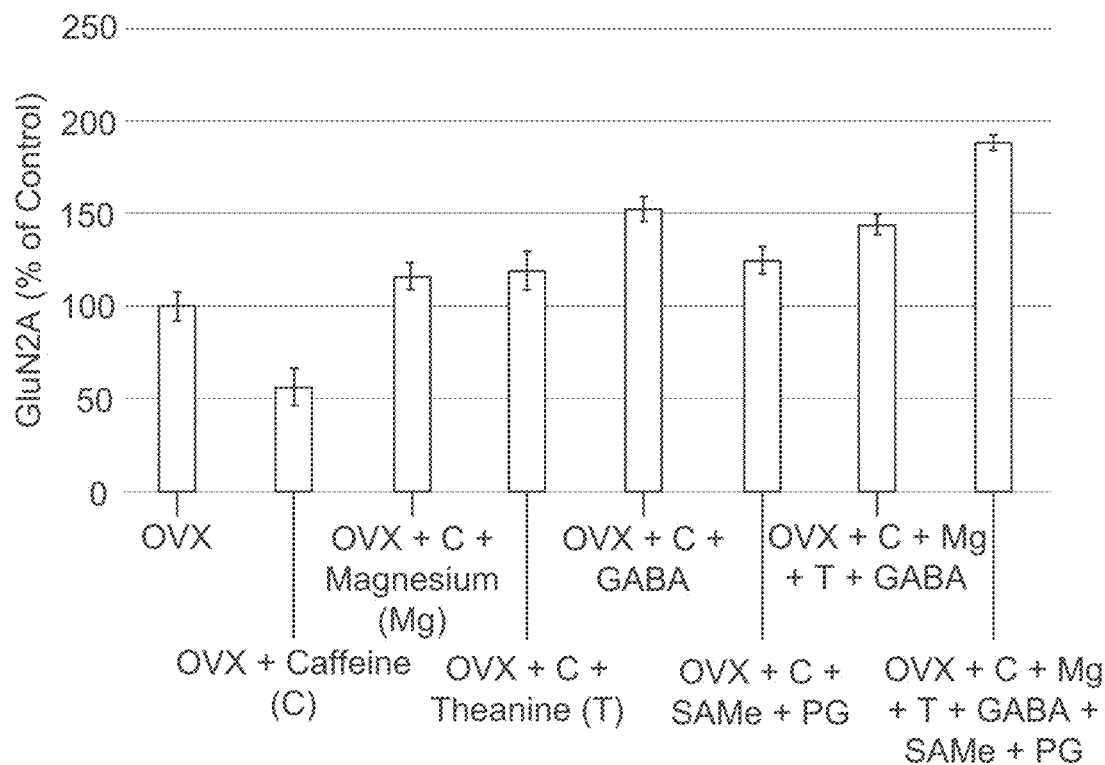
FIG. 2K shows the percentage of GluN2A in OVX female mice, treated with (i) saline (control), (ii) a combination of caffeine (7.5 mg/kg) and saline (caffeine control), (iii) a combination of caffeine (7.5 mg/kg) and 100 mg HED of magnesium glycinate, (iv) a combination of caffeine (7.5 mg/kg) and 200 mg HED of L-theanine, (v) a combination of caffeine (7.5 mg/kg) and 300 mg HED of GABA, (vi) a combination of caffeine (7.5 mg/kg), 150 mg HED of SAMe, and 9 mg HED of propyl gallate, (vii) a combination of caffeine (7.5 mg/kg), 100 mg HED of magnesium glycinate, 200 mg HED of L-theanine, and 300 mg HED of GABA, or (viii) a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 2K shows that the percentage of GluN2A receptor in group 8 was about 180%, unexpectedly much higher than those in groups 1-6, ranging from about 60% to 150%.

To sum up, the results shown in FIGS. 2A-2K demonstrate that the compositions described herein are unexpectedly superior to magnesium, L-theanine, GABA, and SAMe alone in inducing deep sleep.

Example 3

A comparative study was conducted to evaluate the effect of an exemplary composition comprising 100 mg HED of magnesium glycinate, 200 mg HED of L-theanine, 300 mg HED of GABA, 150 mg HED of SAMe, and 9 mg HED of propyl gallate on OVX female mice and male mice.

Both OVX female mice and male mice were divided into three groups: group treated with saline, group treated with 7.5 mg/kg caffeine, and group treated with a combination of 7.5 mg/kg caffeine and the magnesium glycinate, L-theanine, GABA, SAMe and propyl gallate composition. After two hours, the mice were sacrificed under deep anesthesia and their brains were removed. Levels of serum melatonin were measured by ELISA kits. The results are shown in FIG. 3.

Figure 3:
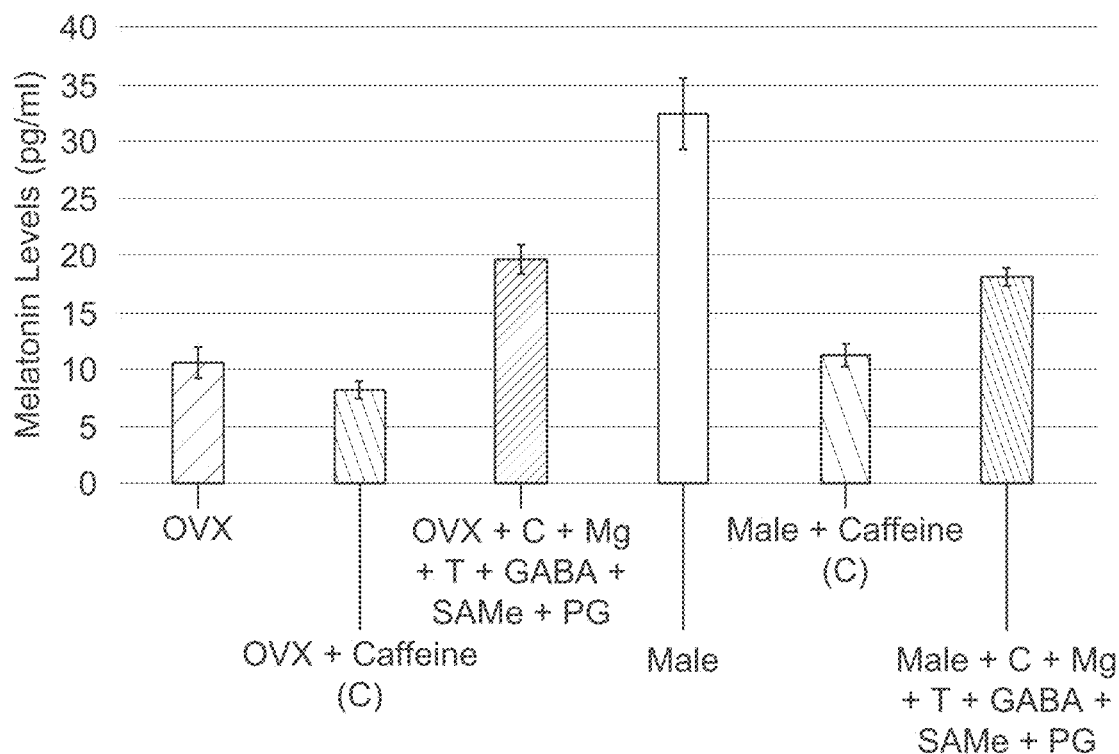
FIG. 3 shows the melatonin levels in OVX female mice and male mice, each treated with saline (control), a combination of caffeine (7.5 mg/kg) and saline (caffeine control), or a combination of caffeine (7.5 mg/kg), 100 mg HED of magnesium glycinate, 200 mg HED of L-theanine, 300 mg HED of GABA, 150 mg HED of SAMe, and 9 mg HED of propyl gallate.

FIG. 3 shows that (i) the melatonin level in the OVX mice treated with caffeine decreased from about 11 μg/ml to about 8 μg/ml and by contrast, the melatonin level in the OVX mice treated with caffeine and the magnesium glycinate, L-theanine, GABA, SAMe and propyl gallate composition was increased from about 11 μg/ml to about 19 μg/ml and (ii) the melatonin level in the male mice treated with caffeine was drastically decreased from about 33 μg/ml to about 12 μg/ml and the melatonin level in these mice treated with caffeine and the magnesium glycinate, L-theanine, GABA, SAMe and propyl gallate composition was decreased from about 33 μg/ml to about 18 μg/ml.

The data demonstrates that the magnesium glycinate, L-theanine, GABA, SAMe and propyl gallate composition is effective in inducing deep sleep in both males and menopausal females, yet, it is more effective in menopausal females. As set forth above, women in general have a much higher risk of insomnia and poor sleep quality than men and menopausal women have worse sleep quality than pre- and post-menopausal women. Therefore, based upon the results obtained from administration of the inventive composition, one can readily conclude that the composition is also highly effective in inducing deep-sleep in pre- and post-menopausal women.

Example 4

A randomized, double-blind, placebo-controlled, parallel study was conducted to evaluate the effectiveness of a composition described herein in influencing sleep compared to a placebo. The composition comprises 150 mg SAMe and 9.0 mg propyl gallate, 300 mg GABA, 200 mg theanine, and 100 mg magnesium glycinate and the placebo comprises microcrystalline cellulose, stearic acid, sodium starch glycolate, and plant-based sources of magnesium stearate coated with Plasacryl T20.

A total of 112 menopausal and perimenopausal women aged 40-65 were enrolled in the study. Prior to the enrollment, the participants were screened for their eligibility ("virtual visit 1"); namely, they were otherwise primarily healthy, but were struggling with sleep (e.g., difficulty in falling asleep, sleeping throughout a night, and falling back asleep). During the screening, each participant's medical information was confirmed for accuracy. Once deemed eligible, the study procedures were explained to the participants, the participants reviewed all questionnaires and were scheduled an End of Study visit ("virtual visit 2"). The participants were then randomly divided into two groups, i.e., the active-treatment group and the control group. From day nine after virtual visit 1, the active-treatment group was orally administered with the composition and the control group was orally administered with the placebo every day about 60 minutes before bed for 3 weeks. On day nine from virtual visit 1, the participants completed their first set of questionnaires which were used as the baselines and every 7 days thereafter. On the day of virtual visit 2, the participants completed their final questionnaires and their medical information was reviewed to ensure no major changes during the study period. The questionnaires included sleep duration and whether the supplement (the composition or placebo) help them fall asleep faster and fall back asleep faster. The questionnaires set forth in the Patient-Reported Outcomes Measurement Information System Sleep-Related Impairment Short Form (PROMIS SRI SF) were used to evaluate episodes of irritable poor sleep. The results are shown in FIGS. 4A-4C.

Figure 4A:
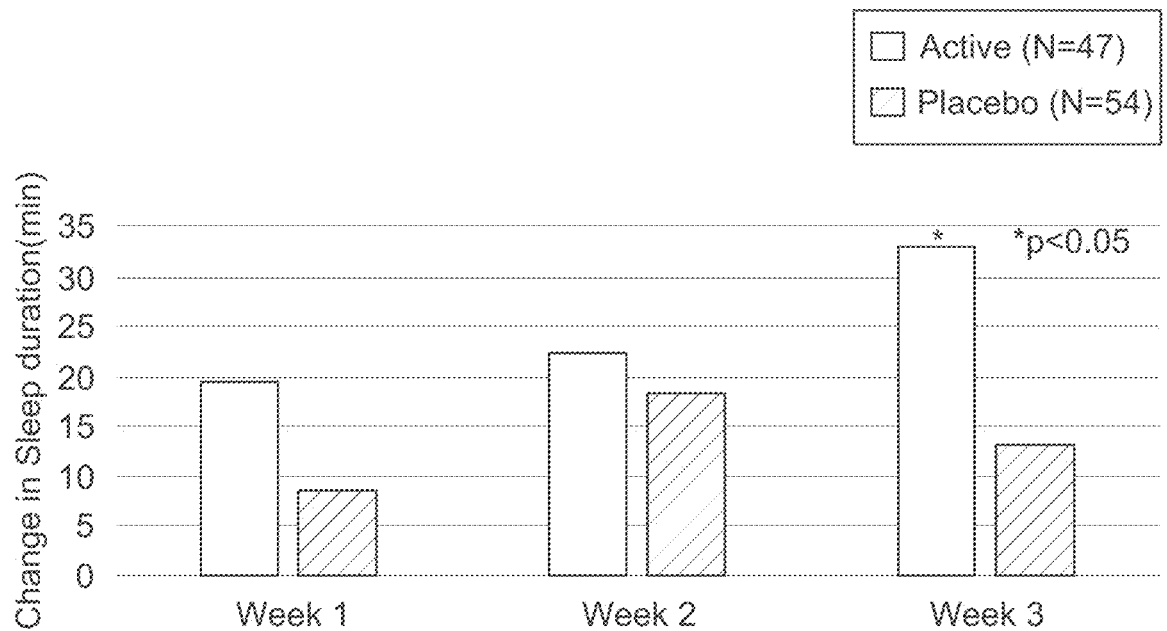
FIG. 4A shows changes in sleep duration on week 1, week 2 and week 3 in women aged 40-65 treated with a composition described herein as compared to those treated with a placebo.
Figure 4B:
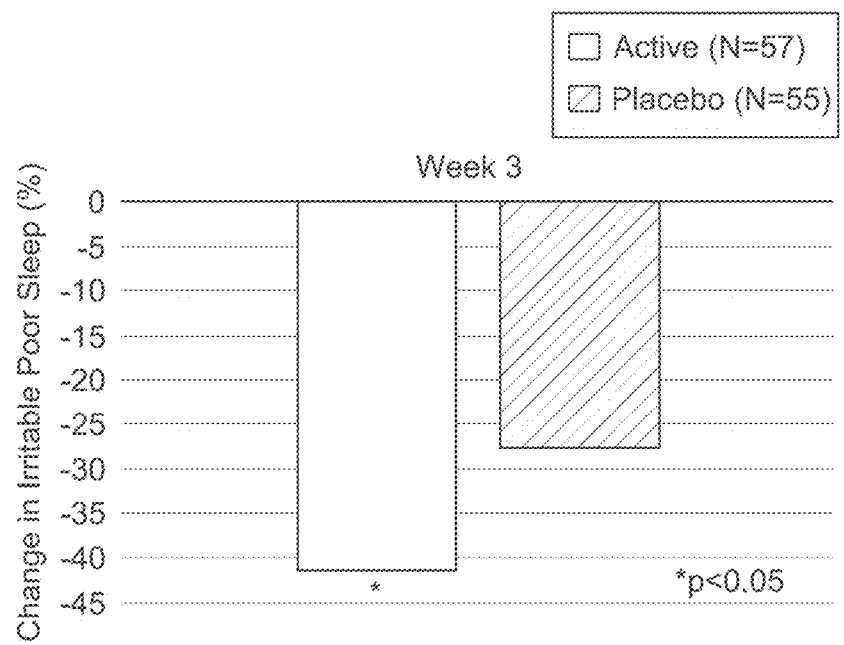
FIG. 4B shows percentage changes of irritable poor sleep from PROMIS SRI validated questionnaires in women aged 40-65 after 3 weeks of consuming a composition described herein as compared to those consuming a placebo.

FIG. 4A shows that, after consuming the composition for three weeks, the group experienced a significant increase in sleep duration by about 33 minutes compared to their baseline, unexpectedly longer than the group consuming the placebo, who experienced an increase in sleep duration by only about 13 minutes compared to their baseline. FIG. 4B shows that, after consuming the composition for three weeks, the group experienced a significant reduction of about 41% in episodes of irritable poor sleep compared to their baseline and by contrast, the placebo group only experienced about 27% reduction in episodes of irritable poor sleep compared to their baseline. The results shown in FIGS. 4A and 4B demonstrate that a composition described herein is effective in improving sleep quality for both menopausal and perimenopausal women.

Figure 4C:
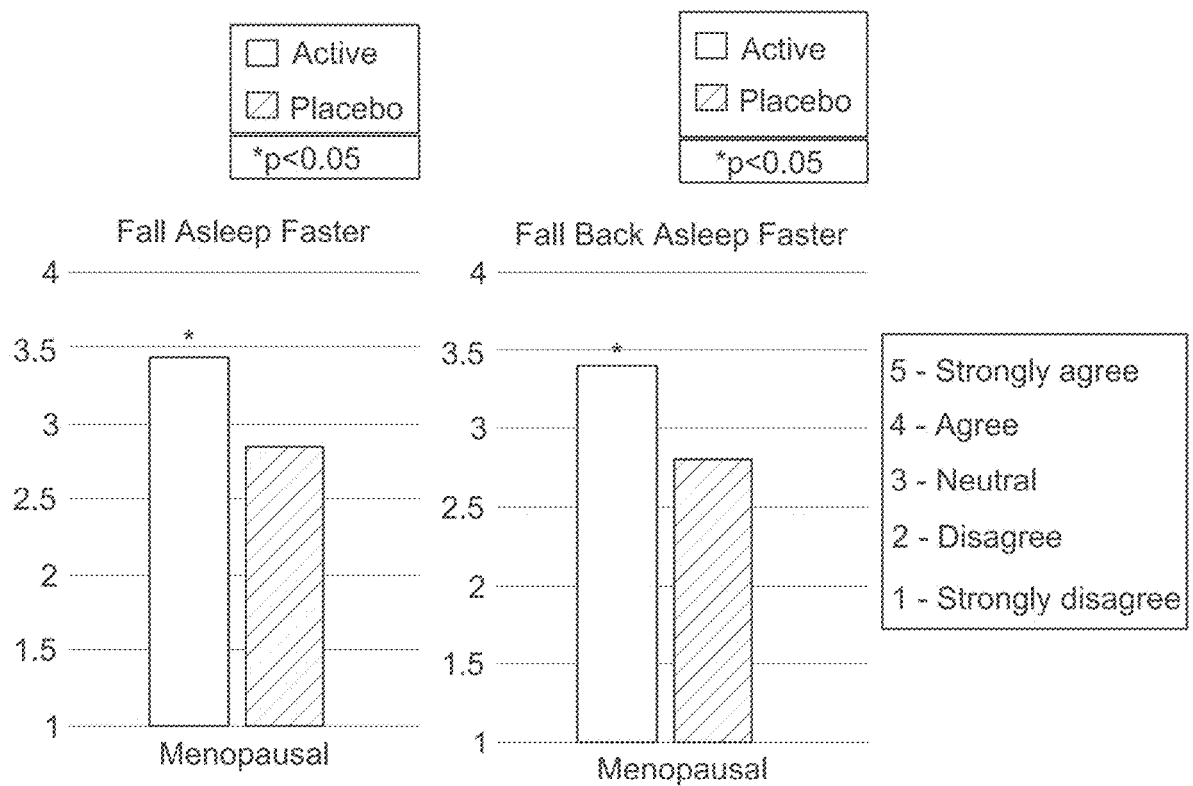
FIG. 4C shows product efficacy results based on the questionnaires of "this product helped me fall asleep faster" and "this product helped me fall back asleep faster" in menopausal women.

FIG. 4C shows the product efficacy in menopausal women after 3 weeks of consuming the composition compared to the placebo. When asking whether the supplement they took help them fall asleep faster and fall back asleep faster if they did wake up, the active-treatment group agreed while the placebo group reported no change or disagreed. The results further demonstrate the efficacy of a composition described herein in improving sleep quality.

Example 5

A clinical study will be carried out to evaluate the effectiveness and safety of compositions described herein in inducing deep sleep in women.

150 mg SAMe and 4.7 mg propyl gallate will be formulated into one tablet containing microcrystalline cellulose, magnesium stearate, water, and titanium dioxide as inactive ingredients. 150 mg GABA, 100 mg L-theanine, and 100 mg magnesium glycinate will be formulated into one capsule containing magnesium stearate, silicon dioxide, microcrystalline cellulose, and gelatin as inactive ingredients.

A total of 60 women will be enrolled into one of three study groups. Group 1 will take one tablet in the morning fasted with about 8 ounces of fluid at approximately the same time each day and take two capsules with about 8 ounces of fluid 60 minutes before bed; group 2 will take one capsule and two capsules with about 8 ounces of fluid 60 minutes before bed; and group 3 will take two capsules with about 8 ounces of fluid 60 minutes before bed. Each group will consume the assigned study products on day 1-29. Each participant will be provided with a heart rate and/or sleep monitor, such as a wearable device like a WhooPR 4.0 to wear throughout the day every day.

Efficacy will be determined by sleep parameters, sleep quality, daytime sleepiness, and quality of life. The sleep parameters will include total sleep time (TST), total wake time (TWT), sleep-onset latency (SLO), light sleep (LS [N1+N2]), deep sleep (DL [N3]), random eye movement (REM), sleep efficiency (SE), wake after sleep onset (WASO), sleep disturbance, and naps. These parameters will be assessed via heart rate and/or sleep monitor such as a wearable device like a Whoop® 4.0 and via morning and evening sleep logs. The sleep quality will be assessed by change from baseline in scores for patient-reported outcomes measurement information system sleep disturbance short form (PROMIS SD SF) and visual analog scale (VAS) sleep quality questionnaire. The daytime sleepiness will be determined by change from baseline in scores for the karolinska sleepiness scale (KSS), which will be assessed every day upon waking up, 11:00 AM, 3:00 PM, and 7:00 PM. The quality of life will be determined by change from baseline in menopause-specific quality of life (MENQOL) scores.

The safety of compositions will be evaluated based on reports of adverse events.

Example 6

Another clinical study will be carried out to evaluate the effectiveness and safety of compositions described herein in inducing deep sleep in women.

100 mg magnesium stearate, 200 mg L-theanine, 300 mg GABA, 400 mg SAMe, and 12.5 mg propyl gallate will be formulated into one tablet containing microcrystalline cellulose, magnesium stearate, water, and titanium dioxide as inactive ingredients. 100 mg magnesium stearate, 200 mg L-theanine, 300 mg GABA, 400 mg SAMe, 12.5 mg propyl gallate, and 100 mg phosphatidyl serine will be formulated into one capsule containing magnesium stearate, silicon dioxide, microcrystalline cellulose, and gelatin as inactive ingredients.

A total of 60 women will be enrolled into one of three study groups. Group 1 will take one tablet in the morning fasted with about 8 ounces of fluid at approximately the same time each day and take two capsules with about 8 ounces of fluid 60 minutes before bed; group 2 will take one capsule and two capsules with about 8 ounces of fluid 60 minutes before bed; and group 3 will take two capsules with about 8 ounces of fluid 60 minutes before bed. Each group will consume the assigned study products on days 1-29. Each participant will be provided with a heart rate and/or sleep monitor, such as a wearable device like a WhooP® 4.0 to wear throughout the day every day.

Efficacy will be determined by sleep parameters, sleep quality, daytime sleepiness, and quality of life. The sleep parameters will include total sleep time (TST), total wake time (TWT), sleep-nnset latency (SLO), light sleep (LS [N1+N2]), deep sleep (DL [N3]), random eye movement (REM), sleep efficiency (SE), wake after sleep onset (WASO), sleep disturbance, and naps. These parameters will be assessed via heart rate and/or sleep monitor such as a wearable device like a Whoop® 4.0 and via morning and evening sleep logs. The sleep quality will be assessed by change from baseline in scores for patient-reported outcomes measurement information system sleep disturbance short form (PROMIS SD SF) and visual analog scale (VAS) sleep quality questionnaire. The daytime sleepiness will be determined by change from baseline in scores for the karolinska sleepiness scale (KSS), which will be assessed every day upon waking up, at 11:00 AM, at 3:00 PM, and at 7:00 PM. The quality of life will be determined by change from baseline in menopause-specific quality of life (MENQOL) scores.

The safety of compositions will be evaluated based on reports of adverse events.

While the present invention has been described in some detail for purposes of clarity and understanding, one will appreciate that various changes in form and detail can be made without departing from the true scope of the invention.

The invention claimed is:

1. A method of improving poor sleep quality in a subject in need thereof, the method comprising:
administering a composition to the subject, wherein the composition comprises an effective amount of two or more sleep-inducing agonists, wherein a first sleep-inducing agonist is L-theanine and a second sleep-inducing agonist is a magnesium salt, wherein L-theanine and the magnesium salt are present in a synergistic ratio of about 2:1 by weight.

2. The method of claim 1, wherein the composition further comprises a sleep-inducing antagonist, wherein the sleep-inducing antagonist is S-adenosyl L-methionine (SAMe).

3. The method of claim 1, wherein the magnesium salt is magnesium glycinate.

4. The method of claim 1, wherein the composition further comprises a third sleep-inducing agonist, wherein the third sleep-inducing agonist is gamma-aminobutyric acid (GABA).

5. The method of claim 4, wherein the composition further comprises a brain-health supporting agent, wherein the brain-health supporting agent is phosphatidylserine.

6. The method of claim 4, wherein the composition further comprises a combination of a sleep-inducing antagonist and a gallic acid ester, wherein the sleep-inducing antagonist is S-adenosyl L-methionine (SAMe).

7. The method of claim 6, wherein the gallic acid ester is propyl gallate.

8. The method of claim 7, wherein the composition further comprises a brain-health supporting agent, wherein the brain-health supporting agent is phosphatidylserine.

9. The method of claim 1, wherein the composition further comprises a combination of a sleep-inducing antagonist and a gallic acid ester, wherein the sleep-inducing antagonist is S-adenosyl L-methionine (SAMe).

10. The method of claim 9, wherein the gallic acid ester is propyl gallate.

11. The method of claim 9, wherein the composition further comprises a brain-health supporting agent, wherein the brain-health supporting agent is phosphatidylserine.

12. The method of claim 2, wherein the composition further comprises propyl gallate.

13. The method of claim 4, wherein the amount of the magnesium salt, the amount of L-theanine, and the amount of GABA are present in a synergistic ratio, wherein the synergistic ratio is about 1:2:3 of the magnesium salt to L-theanine to GABA by weight, respectively.

14. The method of claim 5, wherein the amount of the magnesium salt, the amount of L-theanine, the amount of GABA, and the amount of phosphatidylserine are present in a synergistic ratio, wherein the synergistic ratio is about 1:2:3:1 of the magnesium salt to L-theanine to GABA to phosphatidylserine by weight, respectively.

15. The method of claim 7, wherein the amount of the magnesium salt, the amount of L-theanine, the amount of GABA, and the combined amount of SAMe and propyl gallate are present in a synergistic ratio, wherein the synergistic ratio is about 1:2:3:4.12 of the magnesium salt to L-theanine to GABA to the combination of SAMe and propyl gallate by weight, respectively.

16. The method of claim 8, wherein the amount of the magnesium salt, the amount of L-theanine, the amount of GABA, the combined amount of SAMe and propyl gallate, and the amount of phosphatidylserine are present in a synergistic ratio, wherein the synergistic ratio is about 1:2:3:4.125:1 of the magnesium salt to L-theanine to GABA to the combination of SAMe and propyl gallate to phosphatidylserine, respectively.

17. The method of claim 10, wherein the amount of the magnesium salt, the amount of L-theanine, and the combined amount of SAMe and propyl gallate are present in a synergistic ratio, wherein the synergistic ratio is about 1:2:4.125 of the magnesium salt to L-theanine to the combination of SAMe and propyl gallate by weight, respectively.

18. The method of claim 11, wherein the amount of the magnesium salt, the amount of L-theanine, the combined amount of SAMe and propyl gallate, and the amount of phosphatidylserine are present in a synergistic ratio, wherein the synergistic ratio is about 1:2:4.125:1 of the magnesium salt to L-theanine to the combination of SAMe and propyl gallate to phosphatidyl serine by weight, respectively.

19. The method of claim 1, wherein the poor sleep quality is caused by caffeine.

20. The method of claim 19, wherein the composition is administered to the subject prior to, simultaneously with, or after consuming caffeine-containing drinks, foods, and/or supplements.

21. The method of claim 20, wherein the supplements are caffeine-containing pre-workout supplements.

22. The method of claim 1, wherein the poor sleep quality is caused by menopause.

23. The method of claim 1, wherein the composition is formulated as a single dosage form.

24. The method of claim 1, wherein the composition is administered orally, buccally, or sublingually.

25. The method of claim 1, wherein the composition is administered to the subject orally between 15 minutes and 2 hours before bed.

\* \* \* \* \*